United States Patent
Mann et al.

(10) Patent No.: US 8,630,705 B2
(45) Date of Patent: *Jan. 14, 2014

(54) IMPLANTABLE STIMULATOR

(75) Inventors: Alfred E. Mann, Beverly Hills, CA (US); Tom Xiaohai He, Simi Valley, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 47 days.

This patent is subject to a terminal disclaimer.

(21) Appl. No.: 13/053,031

(22) Filed: Mar. 21, 2011

(65) Prior Publication Data

US 2011/0172739 A1    Jul. 14, 2011

Related U.S. Application Data

(63) Continuation of application No. 11/280,620, filed on Nov. 16, 2005, now Pat. No. 7,920,915.

(51) Int. Cl.
*A61N 1/00* (2006.01)

(52) U.S. Cl.
USPC ............................................................ 607/2

(58) Field of Classification Search
USPC ............. 607/2–3, 36, 37, 45, 46, 57, 61, 116; 600/129, 427, 509
See application file for complete search history.

(56) References Cited

U.S. PATENT DOCUMENTS

| | | |
|---|---|---|
| 3,760,984 A | 9/1973 | Theeuwes |
| 3,845,770 A | 11/1974 | Theeuwes |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |

(Continued)

FOREIGN PATENT DOCUMENTS

| | | |
|---|---|---|
| EP | 1533000 | 5/2005 |
| WO | WO 98/02209 A4 | 1/1998 |

(Continued)

OTHER PUBLICATIONS

Walker et al., "Regulation of Limbic Motor Seizures by GABA and Glutamate Transmission in Nucleus Tractus Solitarius" Epilepsia, 40(8):1051-1057, Aug. 1999 (7 pages).

(Continued)

*Primary Examiner* — Christopher Koharski
*Assistant Examiner* — Roland Dinga
(74) *Attorney, Agent, or Firm* — Vista IP Law Group LLP

(57) ABSTRACT

An implantable stimulator includes a tube assembly that is configured to house a number of components that are configured to apply at least one stimulus to at least one stimulation site within a patient. The tube assembly has a shape that allows the stimulator to be implanted within said patient in a pre-determined orientation. Exemplary methods of stimulating a stimulation site within a patient include applying an electrical stimulation current to a stimulation site via one or more electrodes extending along one or more sides of a stimulator. The stimulator has a shape allowing the stimulator to be implanted within the patient in a pre-determined orientation.

20 Claims, 17 Drawing Sheets

(56) References Cited

U.S. PATENT DOCUMENTS

| | | | |
|---|---|---|---|
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,254,775 A | 3/1981 | Langer | |
| 4,327,725 A | 5/1982 | Cortese et al. | |
| 4,360,019 A | 11/1982 | Portner et al. | |
| 4,487,603 A | 12/1984 | Harris | |
| 4,627,850 A | 12/1986 | Deters et al. | |
| 4,692,147 A | 9/1987 | Duggan | |
| 4,725,852 A | 2/1988 | Gamblin et al. | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,312,439 A | 5/1994 | Loeb | |
| 5,314,451 A | 5/1994 | Mulier | |
| 5,314,458 A * | 5/1994 | Najafi et al. | 607/116 |
| 5,405,363 A | 4/1995 | Kroll et al. | |
| 5,405,367 A | 4/1995 | Schulman et al. | |
| 5,728,396 A | 3/1998 | Peery et al. | |
| 5,782,891 A | 7/1998 | Hassler et al. | |
| 5,948,006 A | 9/1999 | Mann | |
| 6,011,993 A * | 1/2000 | Tziviskos et al. | 607/36 |
| 6,024,704 A | 2/2000 | Meador et al. | |
| 6,051,017 A | 4/2000 | Loeb et al. | |
| 6,061,596 A | 5/2000 | Richmond et al. | |
| 6,164,284 A | 12/2000 | Schulman et al. | |
| 6,175,764 B1 | 1/2001 | Loeb et al. | |
| 6,181,965 B1 | 1/2001 | Loeb et al. | |
| 6,185,452 B1 | 2/2001 | Schulman et al. | |
| 6,185,455 B1 | 2/2001 | Loeb et al. | |
| 6,208,894 B1 | 3/2001 | Schulman et al. | |
| 6,214,032 B1 | 4/2001 | Loeb et al. | |
| 6,234,973 B1 | 5/2001 | Meador et al. | |
| 6,315,721 B2 | 11/2001 | Schulman et al. | |
| 6,368,315 B1 | 4/2002 | Gillis et al. | |
| 6,424,234 B1 | 7/2002 | Stevenson | |
| 6,498,043 B1 | 12/2002 | Schulman et al. | |
| 6,505,401 B1 * | 1/2003 | Doan | 29/860 |
| 6,622,048 B1 | 9/2003 | Mann et al. | |
| 6,631,290 B1 * | 10/2003 | Guck et al. | 600/509 |
| 6,662,035 B2 | 12/2003 | Sochor | |
| 7,132,173 B2 | 11/2006 | Daulton | |
| 7,920,915 B2 | 4/2011 | Mann et al. | |
| 2002/0072778 A1 * | 6/2002 | Guck et al. | 607/36 |
| 2002/0165588 A1 * | 11/2002 | Fraley et al. | 607/37 |
| 2003/0097165 A1 | 5/2003 | Krulevitch et al. | |
| 2003/0236558 A1 | 12/2003 | Whitehurst et al. | |
| 2004/0034394 A1 | 2/2004 | Woods et al. | |
| 2004/0058186 A1 | 3/2004 | Daulton | |
| 2004/0059392 A1 | 3/2004 | Parramon et al. | |
| 2004/0088032 A1 | 5/2004 | Haller et al. | |
| 2004/0147992 A1 | 7/2004 | Bluger et al. | |
| 2004/0220632 A1 | 11/2004 | Burnes | |
| 2005/0137670 A1 * | 6/2005 | Christopherson et al. | 607/122 |
| 2006/0276842 A1 | 12/2006 | He | |
| 2007/0112404 A1 | 5/2007 | Mann et al. | |

FOREIGN PATENT DOCUMENTS

| | | |
|---|---|---|
| WO | WO 02/34332 A1 | 5/2002 |
| WO | WO 2005/105053 | 11/2005 |
| WO | WO 2005/105053 A2 | 11/2005 |
| WO | WO 2007/059343 A2 | 5/2007 |

OTHER PUBLICATIONS

Menetrey, et al. "Spinal and trigeminal projections to the nucleus of the solitary tract: a possible substrate for somatovisceral and viscerovisceral reflex activation", J. Comp. Neurol., Jan. 15, 1987, 255(3): 439-50 (12 pages).

Fanselow, et al., "Reduction of pentylenetetrazole-induced seizure activity in awake rats by seizure-triggered trigeminal nerve stimulation", Journal of Neuroscience, Nov. 1, 2000, 20(21):8160-8168 (9 pages)

Hargreaves, et al. "Pathophysiology of Migraine—New Insights", Canadian Journal of Neurological Sciences, Nov. 1999, 26: Suppl. 3-S12-S19 (8 pages).

Hamel, "Current concepts of migraine pathophysiolgoy", Canadian Journal of Neurological Sciences, vol. 6, Suppl. A, Autumn 1999 (6 pages).

May, et al., "The Trigeminovascular System in Humans: Pathophysiologic Implications for Primary Headache Syndromes of the Neural Influences on the Cerebral Circulation", Journal of Cerebral Blood Flow and Metabolism, 19:115-127, Feb. 1999 (13 pages).

Friedman, et al., "Intraoral Chilling versus Oral Sumatriptan for Acute Migraine", Heart Disease, Nov.-Dec. 2001, 3:357-361 (5 pages).

Salvesen, "Cluster Headache", Current Treatment Options in Neurology, Nov. 1999, 1:441-449 (9 pages).

Headache Classification Committee of the International Headache Society, "Classification and Diagnostic Criteria for Headache Disorders, Cranial Neuralgias and Facial Pain",Cephalalgia 1988;8 Suppl 7:1-96 (86 pages).

Written Opinion of the International Searching Authority dated Aug. 2, 2007 for PCT/US2006/044870, filed Nov. 16, 2008, Applicant: Advanced Bionics Corporation, (4 pages).

International Search Report of the International Searching Authority dated Aug. 2, 2007 from PCT/US06/44870, filed Nov. 16, 2006, Applicant: Advanced Bionics Corporation, Forms PCT/ISA/220 and 210, (3 pages).

Australian Office Action and Search Report dated Nov. 22, 2010 in AU Application No. 2006315285, Applicant: Advanced Bionics Corporation, (11 pages).

European Search Report dated Jul. 28, 2009 for EP Application No. 06 84 4430.6, Applicant: Boston Scientific Neuromodulation Corporation (28 pages).

International Preliminary Report on Patentabiliity dated May 20, 2008 for PCT/US2006/044870, filed Nov. 16, 2006, Applicant: Boston Scientific Neuromodulation Corporation, (1 page).

Supplementary European Search Report dated Jul. 28, 2009 in European Patent Application No. 06844430.6-2305, Applicant: Boston Scientific Neuromodulation Corporation (7 pages).

Medtronic, "New Diagnostic Tool—Reveal? Insertable Loop Recorder" http://www.medtronic.com/reveal/new.html.

Walker et al., "Regulation of limbic motor seizures by GABA and glutamate transmission in nucleus tractus solitarius" Epilepsia, Aug. 1999.

Menetrey, et al. "Spinal and trigeminal projections to the nucleus of the solitary tract: a possible substrate for somatovisceral and viscerovisceral reflex activation", J. Comp. Neurol., Jan. 15, 1987, 255(3): 439-50.

Fanselow, et al., "Reduction of pentylenetetrazole-induced seizure activity in awake rats by seizure-triggered trigeminal nerve stimulation", Journal of Neuroscience, Nov. 2000.

Hargreaves, et al. "Pathophysiology of migraine—new insights", Canadian Journal of Neurological Sciences, Nov. 1999.

Hamel, "Current concepts of migraine pathophysiolgoy", Canadian Journal of Neurological Sciences, Autumn 1999.

May, et al., "The Trigeminovascular System in Humans: Pathophysiologic Implications for Primary Headache Syndromes of the Neural Influences on the Cerebral Circulation", Journal of Cerebral Blood Flow Metabolism, Feb. 1999.

Friedman, et al., "Intraoral Chilling versus Oral Sumatriptan for Acute Migraine", Heart Disease, Nov.-Dec. 2001.

Salvesen, "Cluster Headache", Current Treatment Options in Neurology, Nov. 1999.

International Headache Society, "Classification and Diagnostic Criteria for Headache Disorders, Cranial Neuralgias and Facial Pain", 1988.

\* cited by examiner

IMPLANTABLE STIMULATOR

RELATED APPLICATIONS

The present application is a continuation of U.S. patent application Ser. No. 11/280,620, filed Nov. 16, 2005, which application is herein incorporated by reference in its entirety.

BACKGROUND

A wide variety of medical conditions and disorders have been successfully treated using an implanted stimulator. Such a stimulator will typically stimulate internal tissue, such as a nerve, by emitting an electrical stimulation current according to programmed stimulation parameters.

One class of such implantable stimulators, also known as BION® devices (where BION® is a registered trademark of Advanced Bionics Corporation, of Valencia, Calif.), are typically characterized by a small, cylindrical housing that contains electronic circuitry that produces the desired electric stimulation current between spaced electrodes. These stimulators, also referred to as microstimulators, are implanted proximate to the target tissue so that the stimulation current produced by the electrodes stimulates the target tissue to reduce symptoms or otherwise provide therapy for a wide variety of conditions and disorders.

For example, urinary urge incontinence may be treated by stimulating the nerve fibers proximal to the pudendal nerves of the pelvic floor. Erectile or other sexual dysfunctions may be treated by providing stimulation of the cavernous nerve(s). Other disorders, e.g., neurological disorders caused by injury or stroke, may be treated by providing stimulation to other appropriate nerve(s).

In U.S. Pat. No. 5,312,439, entitled Implantable Device Having an Electrolytic Storage Electrode, an implantable device for tissue stimulation is described. U.S. Pat. No. 5,312,439 is incorporated herein by reference in its entirety.

Another microstimulator known in the art is described in U.S. Pat. No. 5,193,539, "Implantable Microstimulator," which patent is also incorporated herein by reference in its entirety. The '539 patent describes a microstimulator in which power and information for operating the microstimulator are received through a modulated, alternating magnetic field. A coil in the microstimulator is adapted to function as the secondary winding of a transformer. This induction coil receives energy from outside the patient's body and a capacitor is used to store electrical energy which is released to the microstimulator's exposed electrodes under the control of electronic control circuitry.

In U.S. Pat. Nos. 5,193,540 and 5,405,367, which patents are incorporated herein by reference in their respective entireties, a structure and method of manufacture of an implantable microstimulator are disclosed. The microstimulator has a structure which is manufactured to be substantially encapsulated within a hermetically-sealed housing that is inert to body fluids, and of a size and shape capable of implantation in a living body with appropriate surgical tools. Within the microstimulator, an induction coil receives energy or data from outside the patient's body.

In yet another example, U.S. Pat. No. 6,185,452, which patent is likewise incorporated herein by reference in its entirety, there is disclosed a device configured for implantation beneath a patient's skin for the purpose of nerve or muscle stimulation and/or parameter monitoring and/or data communication. Such a device contains a power source for powering the internal electronic circuitry. This power supply is a battery that may be externally charged periodically, e.g., once each day. Similar battery specifications are found in U.S. Pat. No. 6,315,721, which patent is additionally incorporated herein by reference in its entirety.

Other microstimulator systems prevent and/or treat various disorders associated with prolonged inactivity, confinement or immobilization of one or more muscles. Such microstimulators are taught, e.g., in U.S. Pat. No. 6,061,596 "Method for Conditioning Pelvis Musculature Using an Implanted Microstimulator;" U.S. Pat. No. 6,051,017 "Implantable Microstimulator and Systems Employing the Same;" U.S. Pat. No. 6,175,764 "Implantable Microstimulator System for Producing Repeatable Patterns of Electrical Stimulation; U.S. Pat. No. 6,181,965 "Implantable Microstimulator System for Prevention of Disorders;" U.S. Pat. No. 6,185,455 "Methods of Reducing the Incidence of Medical Complications Using Implantable Microstimulators;" and U.S. Pat. No. 6,214,032 "System for Implanting a Microstimulator." The applications described in these additional patents, including the power charging techniques, may also be used with the present invention. The '596, '017, '764, '965, '455, and '032 patents are incorporated herein by reference in their respective entireties.

As will be readily appreciated, a key part of patient treatment using an implanted stimulator is the proper placement of the stimulator such that the stimulation electrodes are proximate to the target tissue to be stimulated. If the stimulation electrodes are optimally placed near the target tissue, stimulation can be affected over a wide range of parameters with optimally minimal power consumption.

SUMMARY

An exemplary implantable stimulator includes a tube assembly that is configured to house a number of components that are configured to apply at least one stimulus to at least one stimulation site within a patient. The tube assembly has a shape that allows the stimulator to be implanted within said patient in a pre-determined orientation.

Exemplary methods of stimulating a stimulation site within a patient include applying an electrical stimulation current to a stimulation site via one or more electrodes extending along one or more sides of a stimulator. The stimulator has a shape allowing the stimulator to be implanted within the patient in a pre-determined orientation.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1:
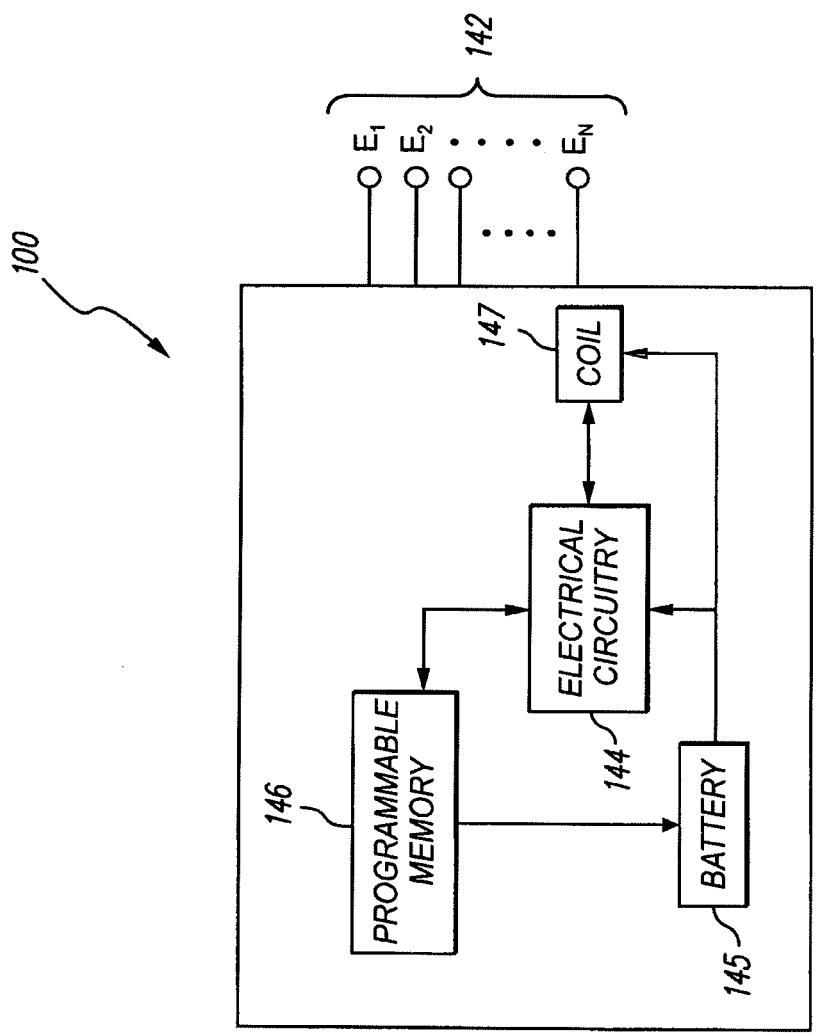
FIG. 1 is a block diagram illustrating a number of components of an exemplary implantable stimulator according to principles described herein.

The present application is related to U.S. patent application Ser. No. 11/142,154, filed Jun. 1, 2005, entitled "Implantable Microstimulator with External Electrodes Disposed on a Film Substrate and Methods of Manufacture and Use," and to a U.S. Patent Application entitled "Methods and Systems for Placing an Implanted Stimulator for Stimulating Tissue" to He et al., Ser. No. 11/232,540, which application was filed on Sep. 21, 2005.

An implantable stimulator having a shape that allows the stimulator to be implanted within a patient in a pre-determined orientation and methods of using such a stimulator are described herein. The stimulator includes a tube assembly, a battery, and a film electrode assembly. The tube assembly is configured to house a number of components that generate at least one stimulus that is applied to at least one stimulation site within a patient. The battery is coupled to the tube assembly and is configured to provide power for the components housed within the tube assembly. The film electrode assembly includes a number of electrodes and is coupled to the stimulator such that the electrodes extend along one or more sides of the stimulator.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As used herein and in the appended claims, the term "stimulator" will be used broadly to refer to any type of device that is implanted to deliver a stimulus to a stimulation site within a patient. As used herein and in the appended claims, unless otherwise specifically denoted, the term "stimulation site" will be used to refer to any nerve, muscle, organ, or other tissue within a patient that is stimulated by an implantable stimulator. For example, in the case of urinary incontinence, the stimulation site may be, but is not limited to, any nerve or muscle in the pelvic floor. Nerves in the pelvic floor region that may be targeted for stimulation include, but are not limited to, the pudendal nerve, pelvic nerve, and the clitoral branches of the pudendal nerve.

The stimulus applied to the stimulation site may include electrical stimulation, also known as neuromodulation. Electrical stimulation will be described in more detail below. The stimulator may additionally or alternatively be configured to infuse therapeutic dosages of one or more drugs into the stimulation site or function in a coordinated manner with a drug delivery system configured to infuse the therapeutic dosages of one or more drugs into the stimulation site. Consequently, as used herein and in the appended claims, the term "stimulus" or "stimulation," unless otherwise indicated, will broadly refer to an electrical stimulation, drug stimulation, or both.

The one or more drugs that may be applied to a stimulation site may have an excitatory effect on the stimulation site. Additionally or alternatively, the one or more drugs may have an inhibitory effect on the stimulation site. Exemplary excitatory drugs that may be applied to a stimulation site include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clonidine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site include at least one or more of the following substances: non-steroidal anti-inflammatory medications (NSAIDS) (e.g., ibuprofen, naproxen, VIOXX); estrogens (e.g., estrone, estradiol, estriol, esters of estradiol, synthetic estrogens such as diethylstilbestrol, quinestrol, chlorotrianisene); progestins (e.g., naturally occurring progesterone, medroxyprogesterone acetate, norethindrone acetate, hydroxyprogesterone acetate, norgestrel, norethindrone); antiestrogens (e.g., clomiphene, tamoxifen); gonadotropin releasing hormone agonist analogues (e.g., leuprolide acetate, nafarelin); androgens (e.g., testosterone, testosterone cypionate, fluoxymesterone, fluoxymesterone, danazol, testolactone); antiandrogens (e.g., cyproterone acetate, flutamide); opioids (e.g., morphine); ziconitide; and/or antidepressants (e.g., serotonin specific reuptake inhibitors and tricyclic antidepressants).

Any of the above listed drugs, alone or in combination, or other drugs developed or shown effective to treat a medical condition or its symptoms may be applied to the stimulation site. In some embodiments, the one or more drugs are infused chronically into the stimulation site. Additionally or alternatively, the one or more drugs may be infused acutely into the stimulation site in response to a biological signal or a sensed need for the one or more drugs.

Turning to the appended drawings, FIG. 1 is a block diagram illustrating a number of components of an exemplary implantable stimulator (100). The components of the stimulator (100) of FIG. 1 may be similar to the components included within a BION® microstimulator (Advanced Bionics® Corporation, Valencia, Calif.), for example. Various details associated with the manufacture, operation, and use of BION implantable microstimulators are disclosed in U.S. Pat. Nos. 5,193,539; 5,193,540; 5,312,439; 6,185,452; 6,164,284; 6,208,894; and 6,051,017 and in U.S. application Ser. No. 10/609,457. All of these listed patents and application are incorporated herein by reference in their respective entireties.

As shown in FIG. 1, the stimulator (100) may include a battery (145), a programmable memory (146), electrical circuitry (144), and a coil (147). The battery (145) is configured to output a voltage used to supply the various components within the stimulator (100) with power. The battery (145) also provides power for any stimulation current applied by the stimulator (100) to the stimulation site. The battery (145) may be a primary battery, a rechargeable battery, a capacitor, or any other suitable power source. Systems and methods for recharging the battery (145), where the battery (145) is rechargeable, will be described below.

The coil (147) is configured to receive and/or emit a magnetic field (also referred to as a radio frequency (RF) field) that is used to communicate with or receive power from one or more external devices that support the implanted stimulator (100), examples of which will be described below. Such communication and/or power transfer may include, but is not limited to, transcutaneously receiving data from the external device, transmitting data to the external device, and/or receiving power used to recharge the battery (145).

The programmable memory unit (146) is used for storing one or more sets of data, for example, stimulation parameters. The stimulation parameters may include, but are not limited to, electrical stimulation parameters and drug stimulation parameters. The programmable memory (146) allows a patient, clinician, or other user of the stimulator (100) to adjust the stimulation parameters such that the electrical stimulation and/or drug stimulation are at levels that are safe and efficacious for a particular medical condition and/or for a particular patient. Electrical stimulation and drug stimulation parameters may be controlled independently. However, in some instances, the electrical stimulation and drug stimulation parameters are coupled, e.g., electrical stimulation may be programmed to occur only during drug stimulation. The programmable memory (146) may be any type of memory unit such as, but not limited to, random access memory (RAM), static RAM (SRAM), a hard drive, or the like.

The electrical stimulation parameters may control various parameters of the stimulation current applied to the stimulation site including, but not limited to, the frequency, pulse width, amplitude, burst pattern (e.g., burst on time and burst off time), duty cycle or burst repeat interval, ramp on time and ramp off time of the stimulation current that is applied to the stimulation site. The drug stimulation parameters may control various parameters including, but not limited to, the amount of drugs infused into the stimulation site, the rate of drug infusion, and the frequency of drug infusion.

Specific electrical stimulation and drug stimulation parameters may have different effects on different types of medical conditions. Thus, in some embodiments, the electrical stimulation and/or drug stimulation parameters may be adjusted by the patient, a clinician, or other user of the stimulator (100) as best serves a particular medical condition. The electrical stimulation and/or drug stimulation parameters may also be automatically adjusted by the stimulator (100), as will be described below. For example, the amplitude of the stimulation current applied to a target nerve may be adjusted to have a relatively low value so as to target relatively large diameter fibers of the target nerve. The stimulator (100) may also increase excitement of a target nerve by applying a stimulation current having a relatively low frequency to the target nerve (e.g., less than 100 Hz). The stimulator (100) may also decrease excitement of a target nerve by applying a relatively high frequency to the target nerve (e.g., greater than 100 Hz). The stimulator (100) may also be programmed to apply the stimulation current to a target nerve intermittently or continuously.

The stimulator (100) is coupled to a number of electrodes $E_1$-$E_n$ (142) configured to apply the electrical stimulation current to the stimulation site. As shown in FIG. 1, there may be any number of electrodes (142) as best serves a particular application. In some examples, one or more of the electrodes (142) may be designated as stimulating electrodes and one of the electrodes (142) may be designated as an indifferent electrode used to complete one or more stimulation circuits. The electrodes (142) will be described in more detail below.

The electrical circuitry (144) is configured to produce electrical stimulation pulses that are delivered to the stimulation site via the electrodes (142). In some embodiments, the stimulator (100) may be configured to produce monopolar stimulation. The stimulator (100) may alternatively or additionally be configured to produce multipolar, e.g., bipolar or tripolar, stimulation. Monopolar electrical stimulation is achieved, for example, using the housing or a portion of the housing of the stimulator (100) as an indifferent electrode. Bipolar or tripolar electrical stimulation is achieved, for example, using one or more of the electrodes (142) as an indifferent electrode.

The electrical circuitry (144) may include one or more processors configured to decode stimulation parameters and generate the corresponding stimulation pulses. In some embodiments, the stimulator (100) has at least four channels and drives up to sixteen electrodes or more. The electrical circuitry (144) may include additional circuitry such as capacitors, integrated circuits, resistors, coils, and the like configured to perform a variety of functions as best serves a particular application.

The drug delivery system described herein may include any of a variety of different mechanisms configured to infuse one or more drugs into the stimulation site. Drug delivery systems based upon a mechanical or electromechanical infusion pump may be used. In other examples, the drug delivery system can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps.

Exemplary pumps or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. All of these listed patents are incorporated herein by reference in their respective entireties.

In some examples, the stimulator (100) is cylindrically shaped. However, because a cylindrical stimulator (100) can easily rotate during and after implantation, the stimulator (100) cannot be implanted with a pre-determined orientation about its central axis. Hence, a single stimulation electrode is often arranged in a ring-like formation about the cylindrical stimulator (100) so that the stimulator (100) can be implanted in any arbitrary orientation. This ring-like arrangement of the electrode causes the electrical field emitted by the stimulator (100) to spread in all 360 degrees of space. In cases where the target tissue or nerve is only located on one side of the stimulator (100), a 360 degree spread of energy is inefficient and reduces the battery life of the stimulator (100) and/or increases the battery recharging frequency of the stimulator (100). Furthermore, additional power may be consumed in attempts to provide effective stimulation, and at some point, the stimulating current may become uncomfortable to the patient if the stimulation current is increased to compensate for the inefficient energy spread.

Figure 2:
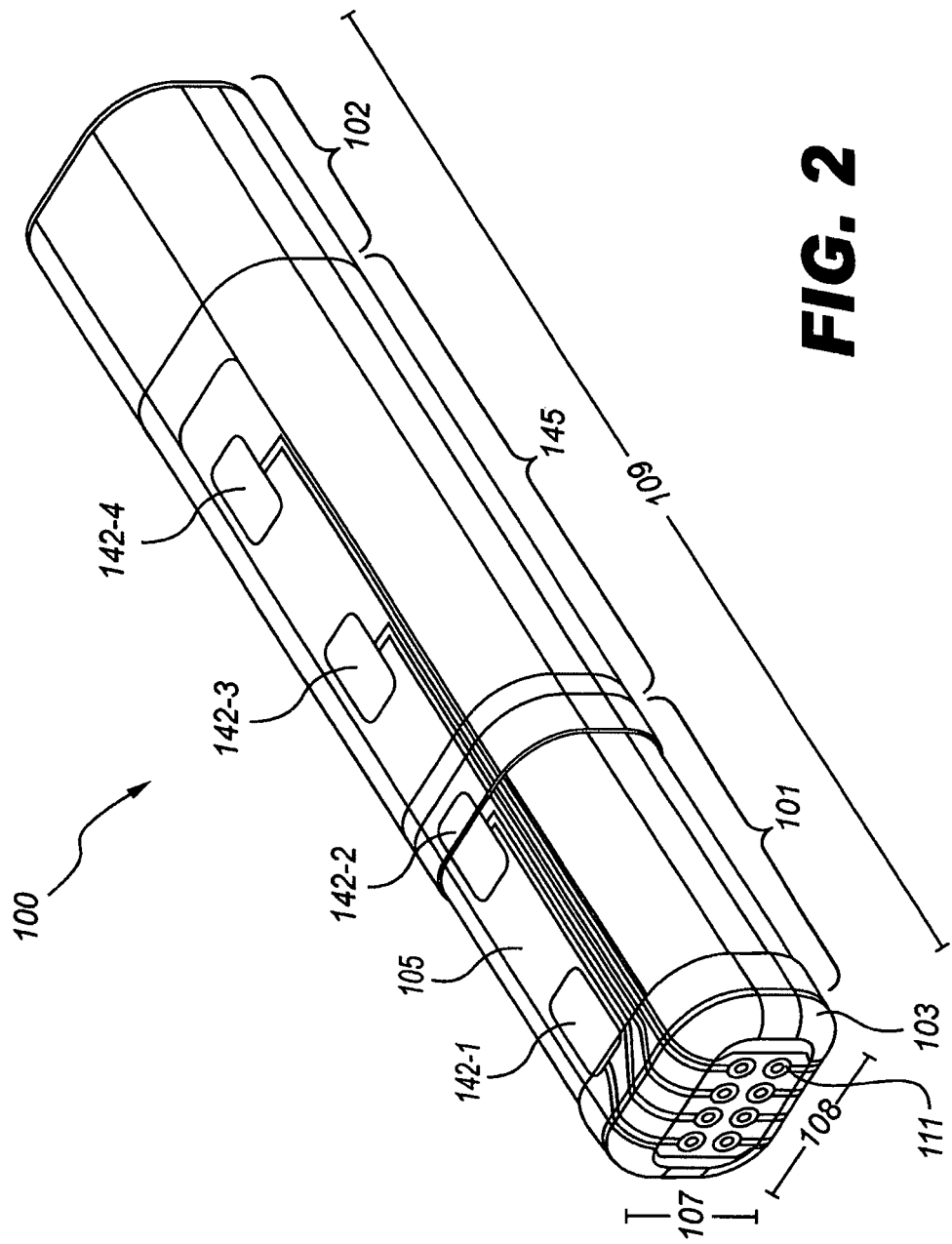
FIG. 2 illustrates an exemplary structure of the implantable stimulator according to principles described herein.

FIG. 2 illustrates an exemplary structure of the implantable stimulator (100). In some embodiments, as shown in FIG. 2, the stimulator (100) has a rectangular cross-section with corner rounding. The rectangular cross-section shape of the stimulator (100) allows the stimulator (100) to be implanted within a patient in a pre-determined orientation. In addition, the slightly significant aspect ratio (cross-section) of the stimulator (100) minimizes the profile, or height (107), of the stimulator (100), which reduces implantation discomfort in many patients. It will be recognized, however, that the rectangular shape of the stimulator (100) shown in FIG. 2 is merely exemplary of the many different dimensional configurations of the stimulator (100). For example, the stimulator (100) may have a long oval shape or any other shape that allows the stimulator (100) to be implanted within the patient in a pre-determined orientation. In general, the stimulator (100) may have any non-cylindrical shape such that the stimulator (100) may be implanted within the patient in a pre-determined orientation.

As shown in FIG. 2, the stimulator (100) has a height (107), width (108), and length (109). An exemplary height (107) is substantially equal to 4.25 millimeters (mm), an exemplary width (108) is substantially equal to 7.25 mm, and an exemplary length (109) is substantially equal to 28 mm. It will be recognized that these dimensions are merely illustrative and that the dimensions of the stimulator (100) may be greater or less than the exemplary dimensions given as best serves a particular application.

In some embodiments, the length (109) of the stimulator (100) is longer than conventional stimulators so that the battery (145) may be relatively larger than batteries in conventional stimulators. A relatively large (145) battery, as will be described in more detail below, increases the battery life of the stimulator (100) and reduces the recharging frequency of the stimulator (100).

The stimulator (100) of FIG. 2 includes a number of components. A ceramic tube assembly (101) is coupled on one end to the battery (145) and on the other end to a feed through assembly (103). The tube assembly (101) houses the electrical circuitry (144; FIG. 1), the programmable memory (146; FIG. 1), the coil (147; FIG. 1), and any other components of the stimulator (100) as best serves a particular application. The feed through assembly (103) includes a number of feed throughs (111) coupled to the electrical circuitry (144; FIG. 1). The feed throughs (111) are also coupled to a film electrode assembly (105) that includes a number of electrodes (142). The stimulator (100) may also include an indifferent electrode (102) coupled to the battery (145). Many of these components will be described in more detail below in connection with FIGS. 3-7.

Figure 3:
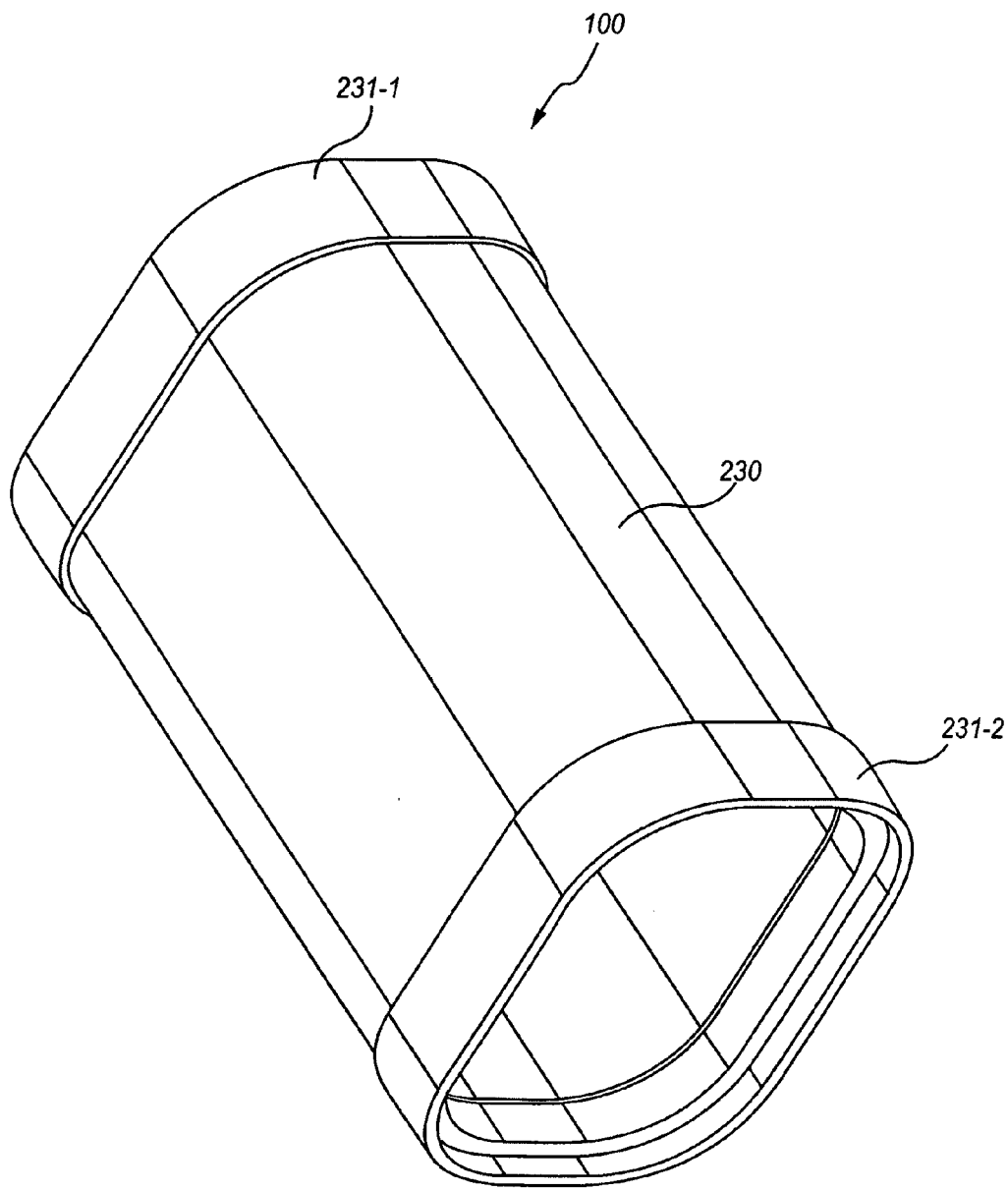
FIG. 3 illustrates an exemplary ceramic tube assembly according to principles described herein.

FIG. 3 illustrates an exemplary tube assembly (101) that can be used in constructing the stimulator (100) of FIG. 2. As shown in FIG. 3, the tube assembly (101) includes a tube (230) with connecting rings (231) at either end. The tube (230) houses the electrical circuitry (144; FIG. 1), the programmable memory (146; FIG. 1), the coil (147; FIG. 1), and any other components of the stimulator (100) as best serves a particular application. The tube (230) may be made out of any suitable material that allows the coil (147; FIG. 1) to emit and receive a magnetic field used to communicate with an external device or with another implanted device. For example, the tube (230) may be made out of a ceramic material, glass, a metal (e.g., Titanium) configured to allow the passage of a magnetic field, or any other suitable material. It will be assumed that the tube (230) is a ceramic tube in the examples given herein for illustrative purposes.

As shown in FIG. 3, the tube (230) has a substantially rectangular cross-section with rounded corners. However, the shape of the tube (230) may vary as best serves a particular application.

A connecting ring (231) is hermetically brazed to both ends of the ceramic tube (231). The connecting rings (231) are used to hermetically seal or couple the ceramic tube assembly (101) to the battery (145; FIG. 2) and to the feed through assembly (103; FIG. 2). The connecting rings (231) may be made out of titanium or any other suitable material (e.g., platinum, iridium, tantalum, titanium nitride, niobium, alloys of any of these, a titanium alloy, etc.) for hermetically sealing the ceramic tube assembly (101) to the battery (145; FIG. 2) and to the feed through assembly (103; FIG. 2). The connecting rings (231) are hermetically brazed to the ceramic tube (231) using any suitable metal brazing process. The connecting rings (231) may additionally or alternatively be made out of metallic materials, glass, ceramic materials, or other biocompatible materials that are connected to the tube (231) using an appropriate process (e.g., brazing, welding, molding, and/or bonding with adhesive).

Figure 4:
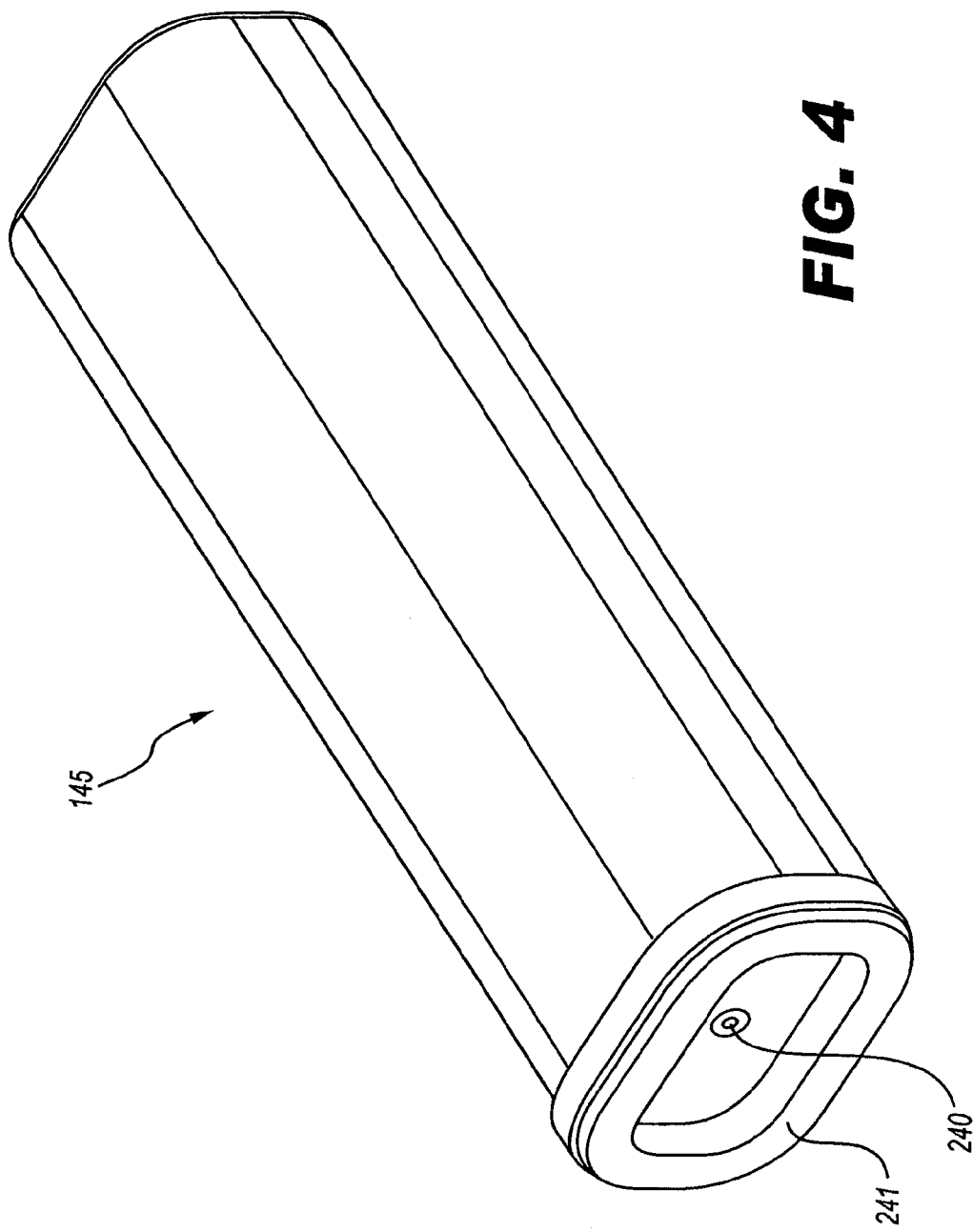
FIG. 4 illustrates an exemplary stimulator battery according to principles described herein.

FIG. 4 illustrates an exemplary battery (145). The battery (145) has a cross section substantially equal to the cross section of the ceramic tube assembly (101; FIG. 3). As previously mentioned, the battery (145) is configured to present an output voltage used to supply power to the various components housed within the ceramic tube assembly (101; FIG. 3). The battery (145) also provides power for any stimulation current applied by the stimulator (100) to a stimulation site. Hence, the battery (145) includes one or more terminals (240) that may be electrically coupled to the electrical components housed within the ceramic tube assembly (101; FIG. 3).

The outer surface of the battery (145) may be made out of any insulative material such as ceramic or glass. The outer surface of the battery (145) may additionally or alternatively be insulated with a non-conductive coating, such as, but not limited to, Parylene™ or Teflon™. A connecting ring (241) is hermetically brazed or otherwise attached to a proximal end of the battery (145). The connecting ring (241) may be made out of titanium or any other material suitable for hermetically attaching the battery (145) to the ceramic tube assembly (101; FIG. 3).

In some alternative embodiments, the outer surface of the battery (145) is made out of a conductive metal (e.g., Titanium). A metal housing allows the casing of the battery to be relatively thin, thereby maximizing the space within the battery casing for battery contents. The metal surface of the battery (145) may be used as an indifferent electrode.

The amount of power or energy that the battery (145) may provide to the various components of the stimulator (100) is substantially proportional to the physical size of the battery (145). Hence, the larger the battery (145), the more power the battery (145) can provide to the components of the stimulator (100; FIG. 2). Some conventional microstimulators have relatively small batteries and therefore for some applications have to be recharged multiple times every day. In some embodiments, the battery (145) of the present stimulator (100; FIG. 2) is relatively larger than batteries found in conventional microstimulators. Therefore, the life of the battery (145) may be up to fifteen times greater or more than the battery life of conventional stimulator batteries. In some examples, the battery (145) of the present stimulator (100; FIG. 2) may for some applications operate up to two weeks or more without having to be recharged.

Figure 5:
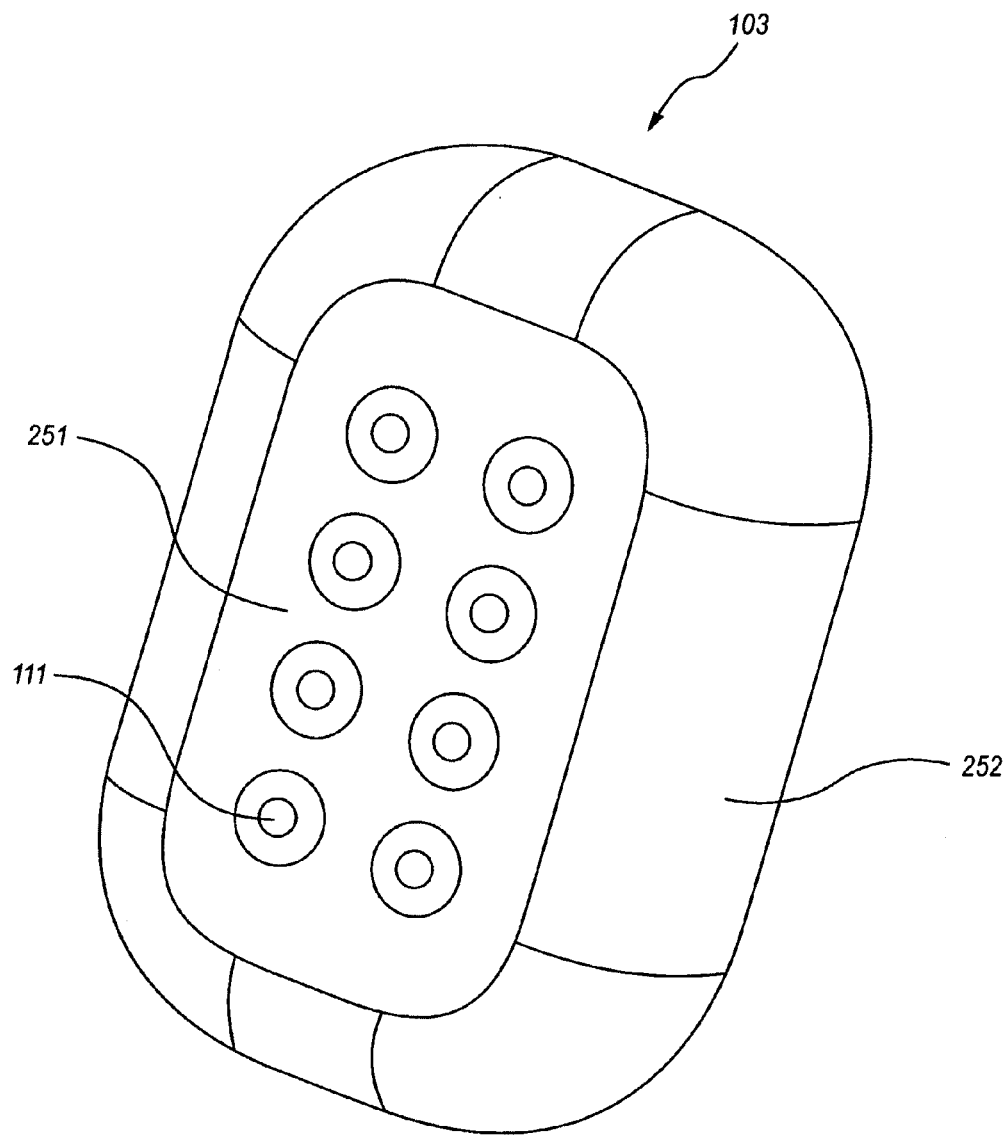
FIG. 5 illustrates an exemplary feed through assembly according to principles described herein.

FIG. 5 illustrates an exemplary feed through assembly (103). The feed through assembly (103) has a cross section substantially equal to the cross section of the ceramic tube assembly (101; FIG. 3). The feed through assembly (103) includes an outer surface or wall (251) made of an insulative material such as ceramic or glass. A connecting ring (252) is hermetically brazed or otherwise attached to the feed through assembly (103). The connecting ring (252) may be made out of titanium or any other suitable material for hermetically attaching the feed through assembly (103) to the ceramic tube assembly (101; FIG. 3).

A number of feed throughs (111), each corresponding to an electrode (142; FIG. 2), are electrically coupled to the outputs of the electrical circuitry (144; FIG. 1) housed within the ceramic tube assembly (101; FIG. 3). In some embodiments, the feed throughs (111) include metal contact pads located on the outer wall (251) that are coupled to metal vias extending through the feed through assembly (103) to an inside wall (not shown) of the feed through assembly (103). These metal vias may be hermetically buried or brazed inside the feed through assembly (103) and electrically coupled to the outputs of the electrical circuitry (144; FIG. 1) housed within the ceramic tube assembly (101; FIG. 3). In this manner, the feed throughs (111) essentially extend the outputs of the electrical circuitry (144; FIG. 1) to the outer surface (251) of the feed through assembly (103). As will be explained in more detail below, the feed throughs (111) are coupled to a number of film electrodes (FIG. 2) that may be selectively controlled by the electrical circuitry (144; FIG. 1) housed within the ceramic tube assembly (101; FIG. 3).

Figure 6:
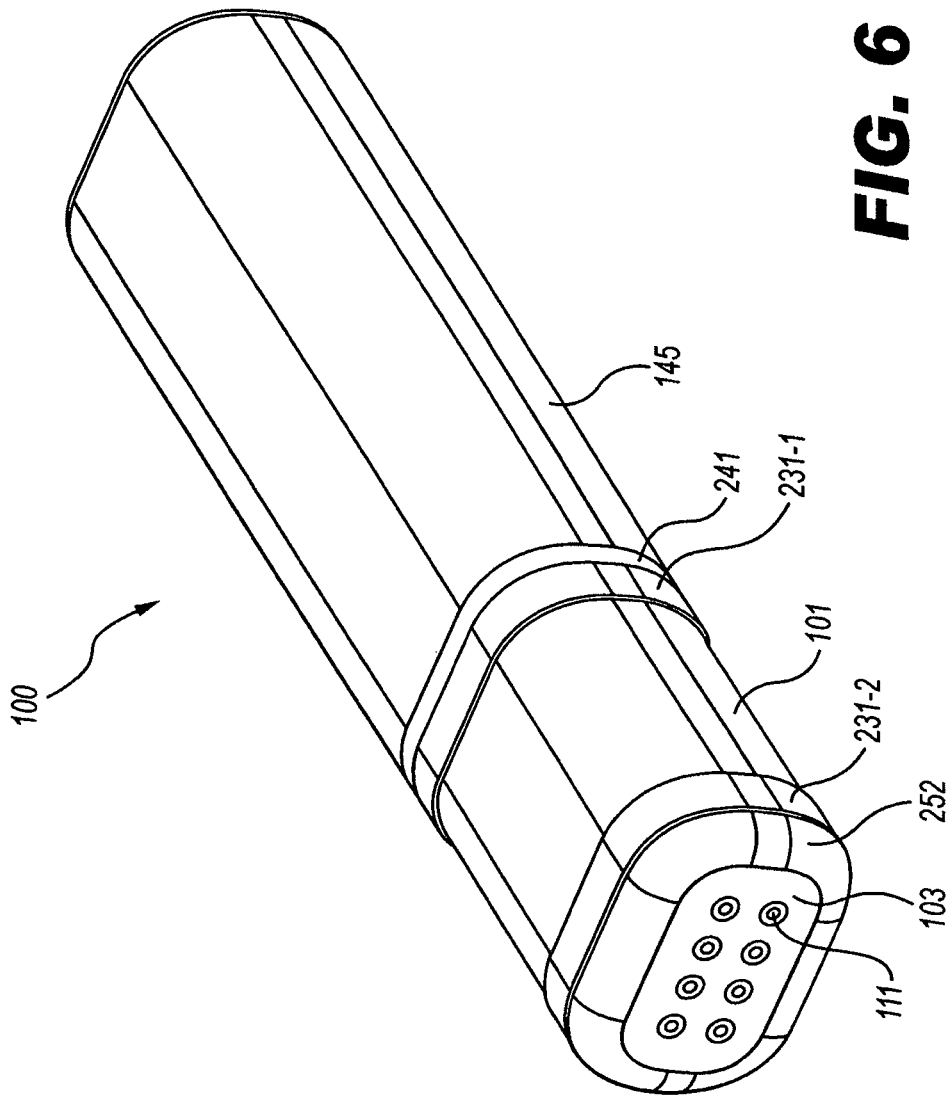
FIG. 6 shows the feed through assembly, ceramic tube assembly, and battery laser-welded together to form a sealed hermetic enclosure for the stimulator according to principles described herein.

FIG. 6 shows the feed through assembly (103), ceramic tube assembly (101), and battery (145) laser welded together to form a sealed hermetic enclosure for the stimulator (100). The connecting ring (241) of the battery (145) is laser welded to the connecting ring (231-1) of the ceramic tube assembly (101) and the connecting ring (252) of the feed through assembly (103) is laser welded to the connecting ring (231-2) of the ceramic tube assembly (101). It will be recognized that the laser welding may include or be replaced by any suitable technique for hermetically coupling the connecting rings (241, 252, 231), including forming a mechanical and electrical bond with a conductive adhesive, such as an epoxy.

Figure 7:
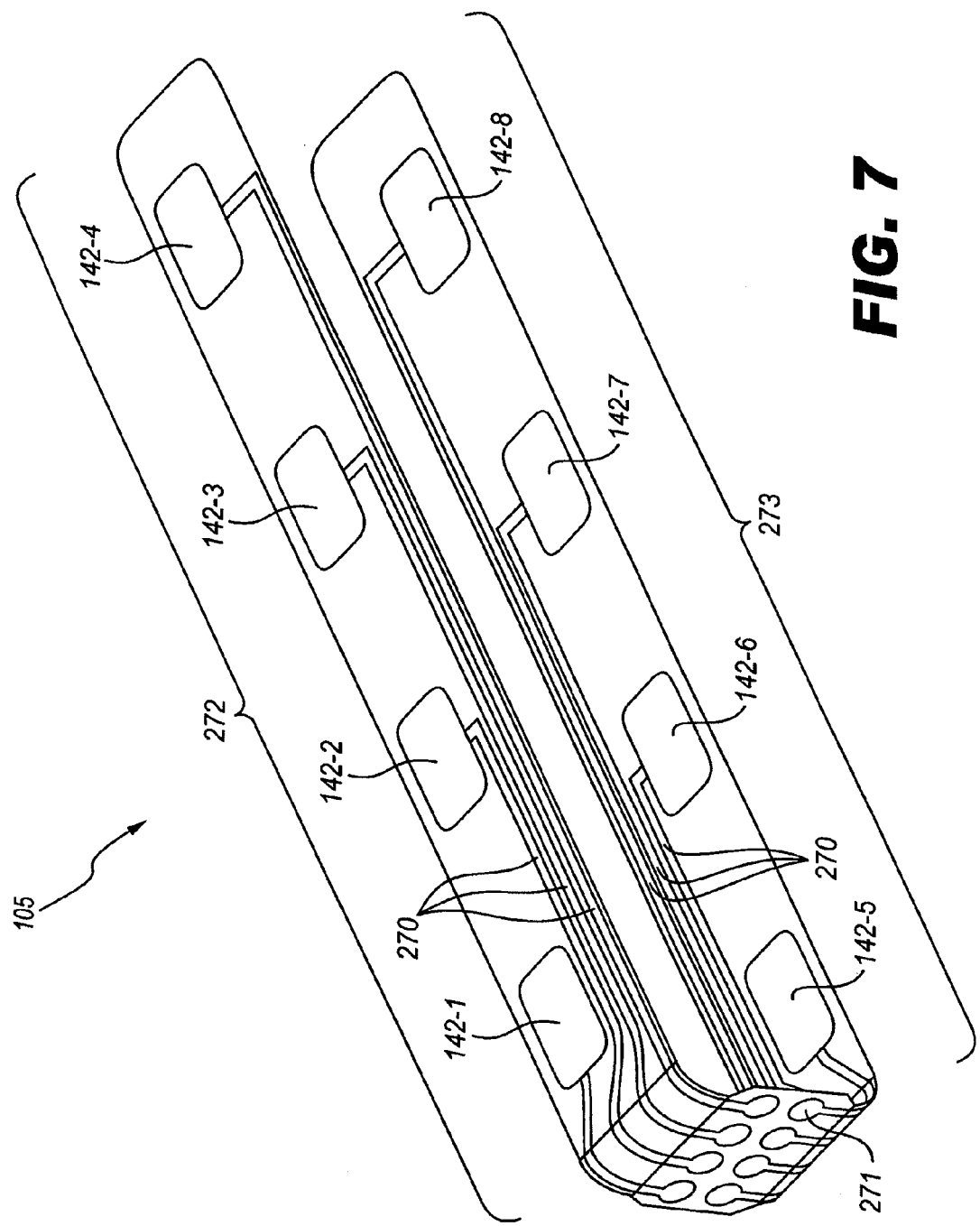
FIG. 7 illustrates an exemplary film electrode assembly according to principles described herein.

FIG. 7 illustrates an exemplary film electrode assembly (105). The film electrode assembly (105) is made out of a polymer film or any other suitable material and includes a number of film electrodes (142). The polymer film may be any thickness as best serves a particular application. Eight film electrodes (142) are shown in FIG. 7 for illustrative purposes only. There may be more or less than eight film electrodes (142) as best serves a particular application.

Each film electrode (142) is coupled to one of the feed throughs (111; FIG. 2) via a metal trace (270). Each metal trace (270) is deposited on the film electrode assembly (105) using any suitable technique, such as sputtering. The metal traces (270) are covered or insulated by a thin film of polymer that is deposited after the metal traces (270) are deposited on the film electrode assembly (105).

The feed through assembly (105) may also include a number of metal contacts (271). The metal contacts (271) are positioned to make contact with the feed throughs (111; FIG. 2) to form a conductive path from the feed throughs (111; FIG. 2) to the electrodes (142). Chemical etching or lithographic techniques may be used to open areas on the traces (270) to expose the metal to form the electrodes (142) and the metal contacts (271). It will be recognized that the electrodes (142) and metal contacts (271) may be made using any suitable method or technique. The physical dimensions of the electrodes (142) and the metal contacts (271) may vary as best serves a particular application.

It will be noted that the film electrode assembly (105) is merely exemplary of the many possible electrode configurations that may be used with the exemplary stimulator (100) described herein. For example, one or more leads having a number of electrodes may alternatively or additionally be coupled to the stimulator (100).

Figure 8:
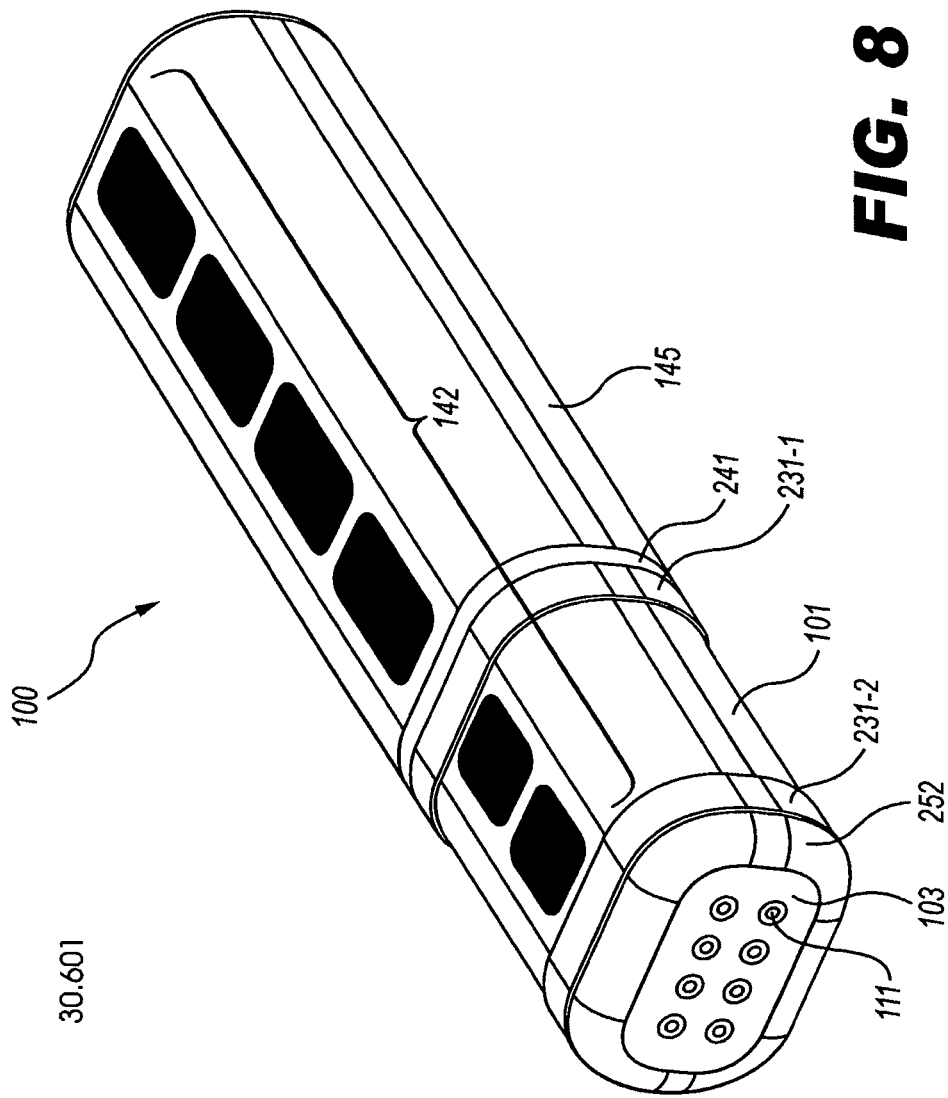
FIG. 8 illustrates an exemplary stimulator wherein the electrodes are coupled directly to the surface of the stimulator according to principles described herein.

Alternatively, the electrodes (142) may be coupled directly to the surface of the stimulator (100). For example, FIG. 8 illustrates an exemplary stimulator (100) wherein the electrodes (142) are coupled directly to the surface of the stimulator (100). The electrodes (145) may be disposed on any portion of the stimulator (100) and, in some examples, may be selectively configured to act as cathodes or anodes.

As shown in FIG. 7 and in FIG. 2, the film electrode assembly (105) is configured to wrap around one or more sides of the body of the stimulator (100; FIG. 2) such that the electrodes (142) are aligned along one or more sides of the body of the stimulator (100; FIG. 2). In some embodiments, the film electrode assembly (105) includes a top extending member (272) and a bottom extending member (273) each including a number of electrodes (142). For example, the top extending member (272) of the film electrode assembly (105) shown in FIG. 7 includes four electrodes (142-1 through 142-4). Likewise, the bottom extending member (273) of the film electrode assembly (105) includes four electrodes (142-5 through 142-8). However, the film electrode assembly (105) may alternatively only include one extending member (e.g., the top extending member (272)).

In yet another alternative embodiment, the film electrode assembly (105) includes more than two extending members. These multiple extending members may be aligned along any side of the body of the stimulator (100; FIG. 2). For example, the film electrode assembly (105) may include four extending members that extend along all four sides of the stimulator (100; FIG. 2). Each of the four extending members may include one or more electrodes (142).

The film electrode assembly (105) may be coupled to the body of the stimulator (100) using a medical adhesive or any other suitable attachment material or device. The film electrode assembly (105) is aligned such that the metal contacts (271) make contact with the feed throughs (111; FIG. 2). Mechanical pressure may be applied, if needed, to ensure that the metal contacts (271) make sufficient contact with the feed throughs (111; FIG. 2).

In some embodiments, each of the electrodes (142) may be selectively controlled. In other words, the electrical stimulation parameters may be adjusted or programmed to control the stimulation current output via each of the electrodes (142). For example, if the electrode (142-4) shown in FIG. 2 is nearest the desired stimulation site, the electrical stimulation parameters may be adjusted such that stimulation current is only delivered via electrode (142-4). By selectively applying stimulation current via any one of the electrodes (142), a number of different stimulation therapies may be applied to a patient.

In addition, the electrical field emitted by the electrodes (142) may be more efficiently directed towards a desired stimulation site by using the stimulator configuration described in connection with FIGS. 2-8 as opposed to using a cylindrically shaped stimulator with ring-like electrodes. For example, the stimulation parameters may be programmed such that only the electrodes (142-1 through 142-4) included in the top extending member (272; FIG. 7) emit an electrical current. In this manner, the electrical stimulation current is only emitted from one side of the stimulator (100), as opposed to being emitted in all 360 degrees of space.

The stimulator configuration described in connection with FIGS. 2-8 also facilitates the proper implantation and placement of the stimulator (100). Because the stimulator (100) is configured to be able to selectively apply electrical stimulation current to any of a number of locations via the multiple electrodes (142), the stimulator (100) may be implanted in a location that is only approximately near the desired stimulation site. The patient or clinician may then activate the electrode(s) closest to the desired stimulation site.

The stimulator (100) of FIG. 2 may be implanted within a patient using any suitable surgical procedure such as, but not limited to, injection, small incision, open placement, laparoscopy, or endoscopy. The stimulator (100) may be implanted within a patient with a surgical tool such as a hypodermic needle, bore needle, or any other tool specially designed for the purpose. In general, the stimulator (100) is implanted with a tool that is used to push the stimulator (100) through a needle, cannula or incision to a position proximate to the target tissue to be stimulated.

For example, a tool used to implant a stimulator (100) may be an elongated, tubular, rigid or semi-rigid tool with a handle at one end and some mechanism at the tip for engaging the stimulator. The engagement mechanism at the tip holds the stimulator in place on the tool until released. With the stimulator engaged by the tool, the tool is used to push the stimulator into place.

In some instances, it may be difficult, however, to accurately position the stimulator (100) with this push insertion method. The clinician placing the stimulator (100) often pushes the stimulator (100) through resistive tissue using the handle of the insertion tool. Any slight movement of the hand during this procedure can produce a significant direction shift at the tool tip, possibly resulting in a placement of the stimulator (100) relatively distant from a desired implant location and target tissue.

Additionally, when the stimulator (100) is finally positioned, the mechanism engaging the stimulator (100) is released. The act of releasing the stimulator (100) may also affect the position of the stimulator (100). If the position of the stimulator (100) shifts after the tool has been disengaged, it may be difficult to reposition the stimulator (100).

There are some locations in the human body where a stimulator (100) would be implanted, such as in a limb or in the neck, where a needle can be inserted, passed proximal to the target tissue to be stimulated and then exit through the skin. A line (e.g., fine wire or thread) can be attached to this pass-through needle so as to then pass through the patient proximal to the target tissue for stimulation. A stimulator (100) is then attached to this line which is used to pull the stimulator (100) into place proximal to the target tissue to be stimulated within the patient. This process will be illustrated and described in detail below.

Figure 9:
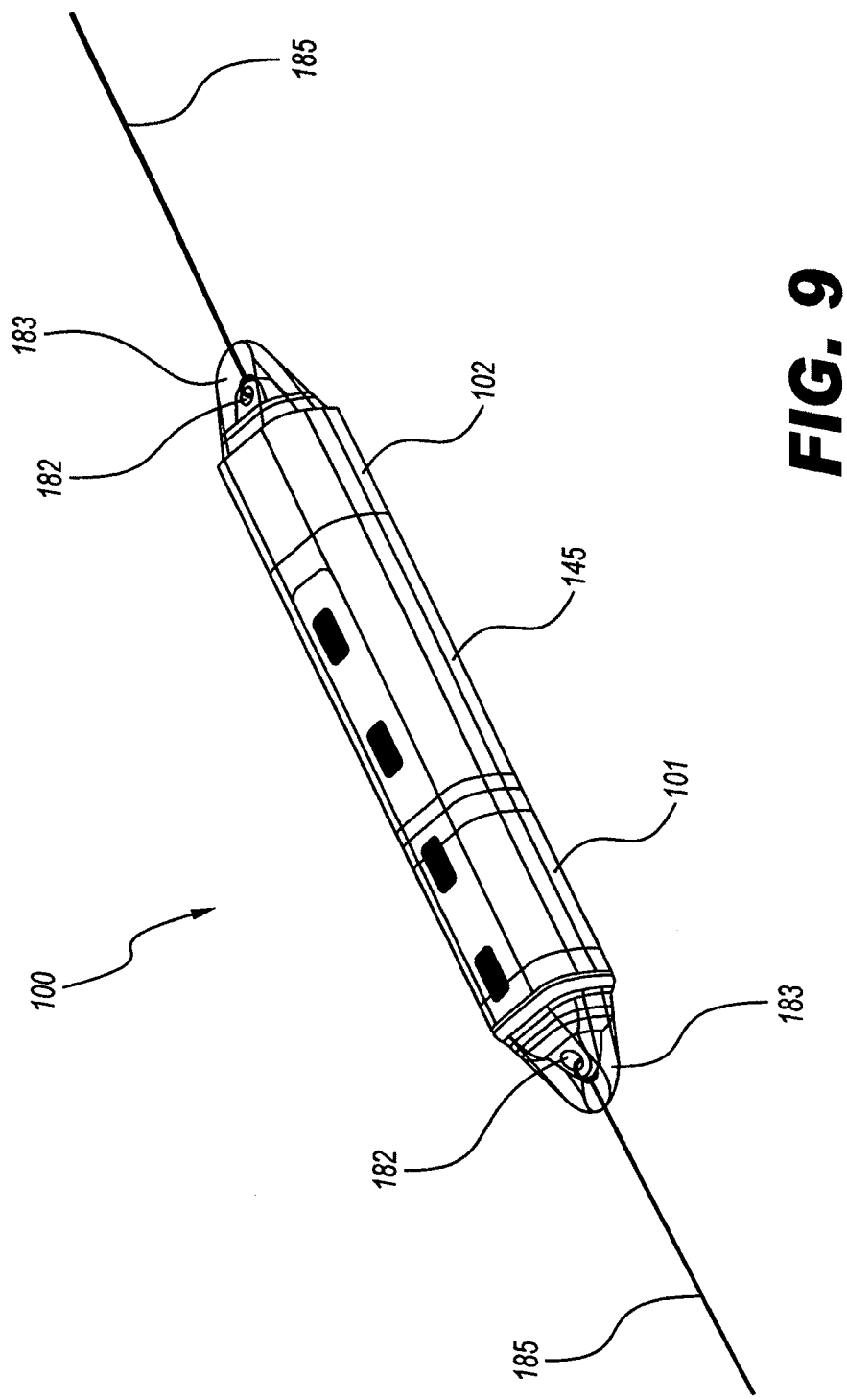
FIG. 9 illustrates an exemplary stimulator according to principles described herein which is adapted to be easily and readily positioned at an optimal location in a patient according to principles described herein.

Turning to FIG. 9, at either end of the stimulator (100) an eyelet (182) is formed. A line (185) is then attached to the eyelet (182) at either or both ends of the stimulator (100). This line may be any line that can be pulled through a portion of a patient's body and then used to position the stimulator (100) as described herein. For example, the line (185) may be, but is not limited to, a string, a suture line, a silk line, a wire, a filament and the like. In some examples, the line is dissolvable, meaning that the line will naturally dissolve if left in the patient's tissue.

Alternative to the eyelets (182), any other means of attaching or anchoring the line (185) to the stimulator (100) may be used. For example, the line may be tied to the eyelet (182), integrated into the stimulator (100) itself, tacked or adhered to the stimulator (100), etc.

Each attachment point of the line (185) to the stimulator (100) may be encapsulated. For example, a polymer cap (183) of, for example, silicone may be placed over the attachment points where the line (185) is secured to the stimulator (100).

Figure 10:
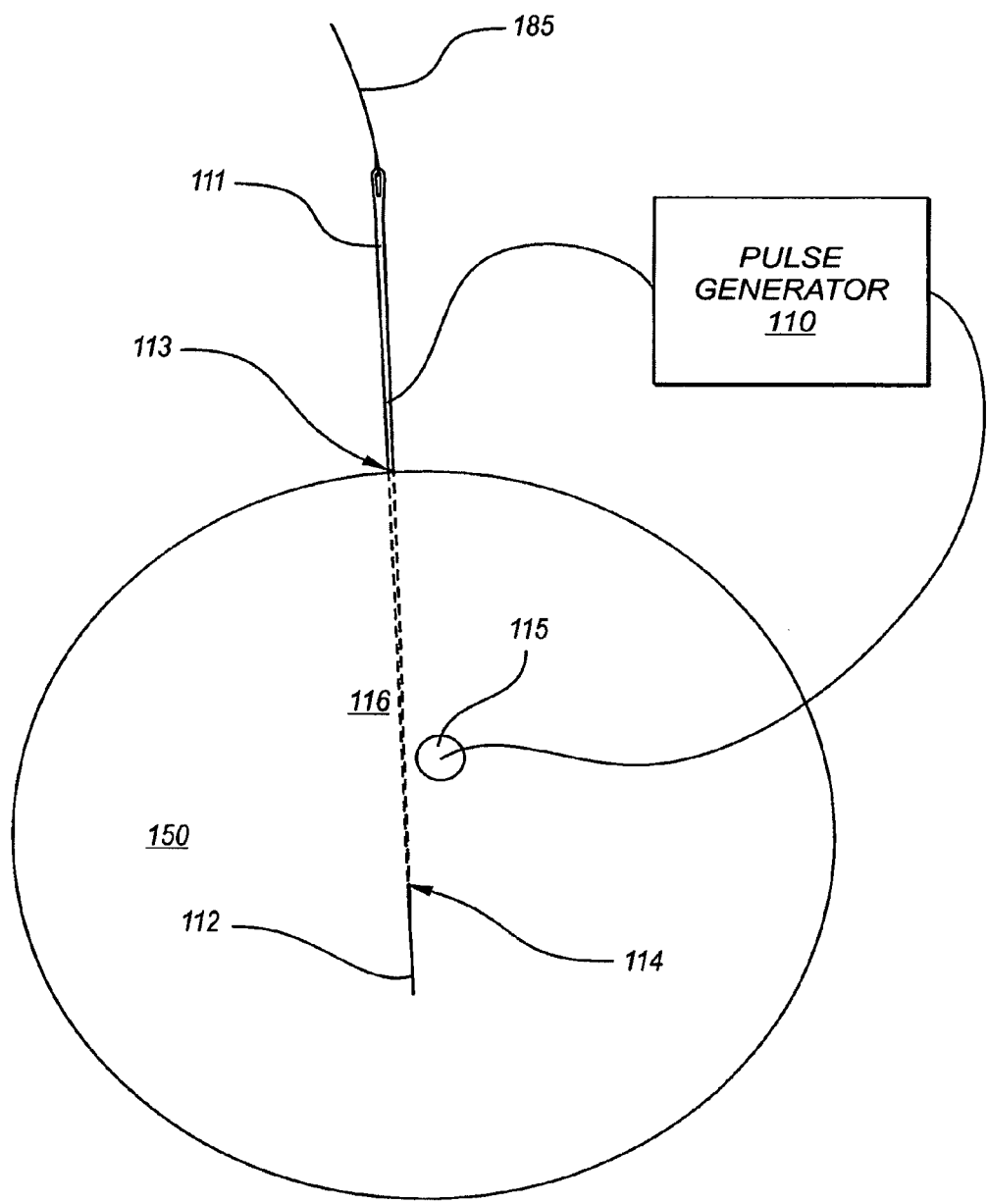
FIGS. 10-12 illustrated various steps in an exemplary method of implanting a stimulator proximal to a stimulation site according to principles described herein.
Figure 11:
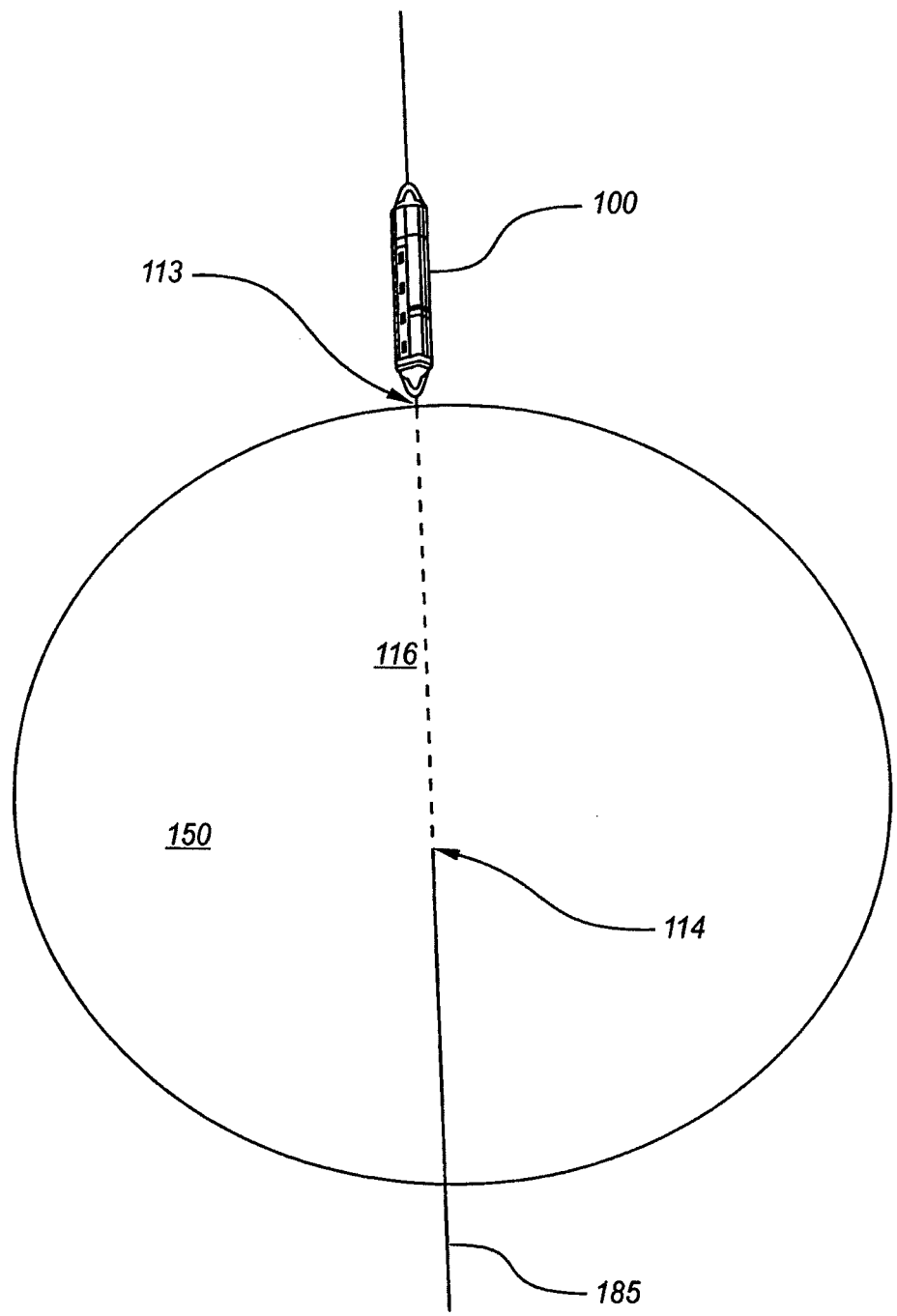

An exemplary method of implanting the stimulator (100) of FIG. 9 will now be described with reference to FIGS. 10-12. In FIG. 10, the body (150) represents a portion of the human body where tissue targeted for stimulation (i.e., a stimulation site) is located between a needle insertion point and a needle exit point as will be described herein. Consequently, the body (150) may represent, for example, a patient's neck or limb or some other location relatively near the surface under a patient's skin.

As shown in FIG. 10, a needle (111), to which the line (185) is attached, has a sharp tip (112) that is threaded through the patient's body between an insertion point (113) and an exit point (114). The needle (111) is inserted through an insertion point (113) in the patient's body (150). The needle (111) is then passed proximal to the stimulation site (also referred to as target tissue) (116) that is targeted for stimulation. The tip (112) of the needle (111) then exits the patient's body (150) through an exit point (114).

As the needle (111) is threaded between the insertion point (113) and exit point (114), it may be useful to confirm that the needle (111) has been inserted proximal to the stimulation site (116) as intended. Consequently, an electrical pulse generator (110) may be electrically connected to the needle (111) as shown in FIG. 10. The pulse generator (110) is also connected to an indifferent electrode (115) that may be placed on the patient's skin near to the stimulation site (116).

The pulse generator (110) is then used to provide an electrical stimulation pulse through the needle (111) to the stimulation site (116). The needle (111) is made of metal or some other electrically conductive material so as to conduct the electrical stimulation pulse from the pulse generator (110). In some examples, most of the length of the needle is covered with an insulating material and only the tip (112) delivers the electrical stimulation pulse to the surrounding tissue. If the needle (111) is properly placed, the stimulation pulse from the pulse generator (110) will cause a predictable effect that should result from stimulation of the stimulation site (116), for example, a paresthesia. The patient can be questioned or otherwise monitored as to the effect created by the pulse generator (110) so as to confirm the proper placement of the needle (111). In this way, it can be ascertained that the needle (111) has been inserted proximal to the tissue (116) to be stimulated.

The needle (111) is then pulled through the exit point (114) leaving the line (185) threaded through the body (150) and running next to the target tissue (116). As shown in FIG. 11, the stimulator (100) is attached to the line (185) outside the insertion point (113). The portion of the line (185) extending from the exit point (114) is then pulled to pull the stimulator (100) though the insertion point (113) and through the patient's body (150) to a position proximal to the tissue (116) targeted for stimulation.

Figure 12:
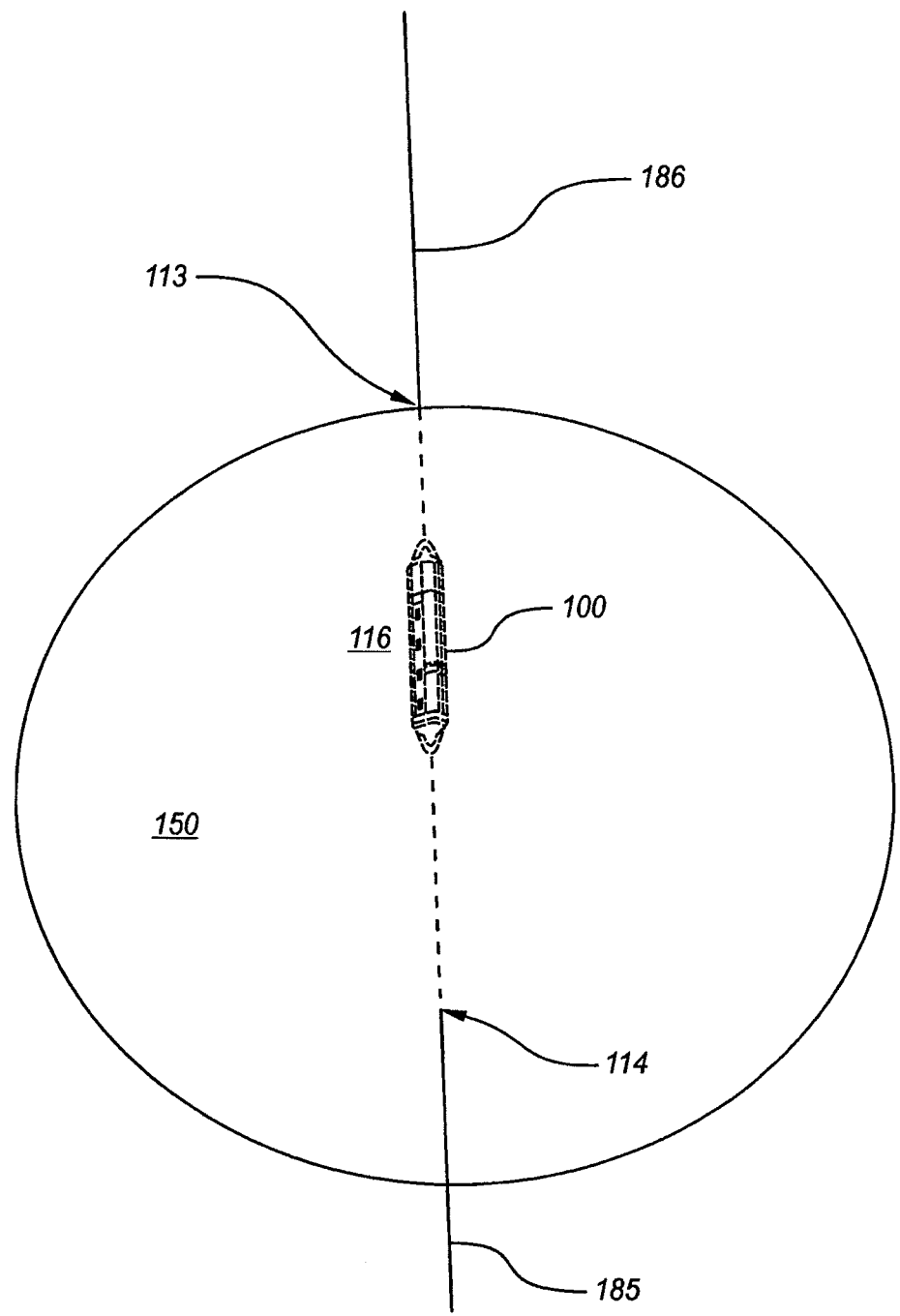

FIG. 12 illustrates the stimulator (100) positioned inside the body (150) proximal to the tissue (116) targeted for stimulation. As shown in FIG. 12, a second line (186) is attached to the other end of the stimulator (100) and extends from the insertion point (113) even after the stimulator (100) has been pulled into the patient's body (150). Consequently, if the stimulator (100) is pulled too far into the patient's body (150) using the line (185) extending from the exit point (114), past the tissue (116) targeted for stimulation, the clinician placing the stimulator (100) can pull the stimulator (100) back into the optimal placement by pulling on the second line (186). In fact, the clinician can pull on either line (186, 185) as needed, with a flossing action, to determine and obtain the optimal placement for the stimulator (100). During this process, the stimulator (100) may be active and providing an electrical stimulation about which the patient can be questioned or monitored to determine the most efficacious placement for the stimulator (100).

Figure 13:
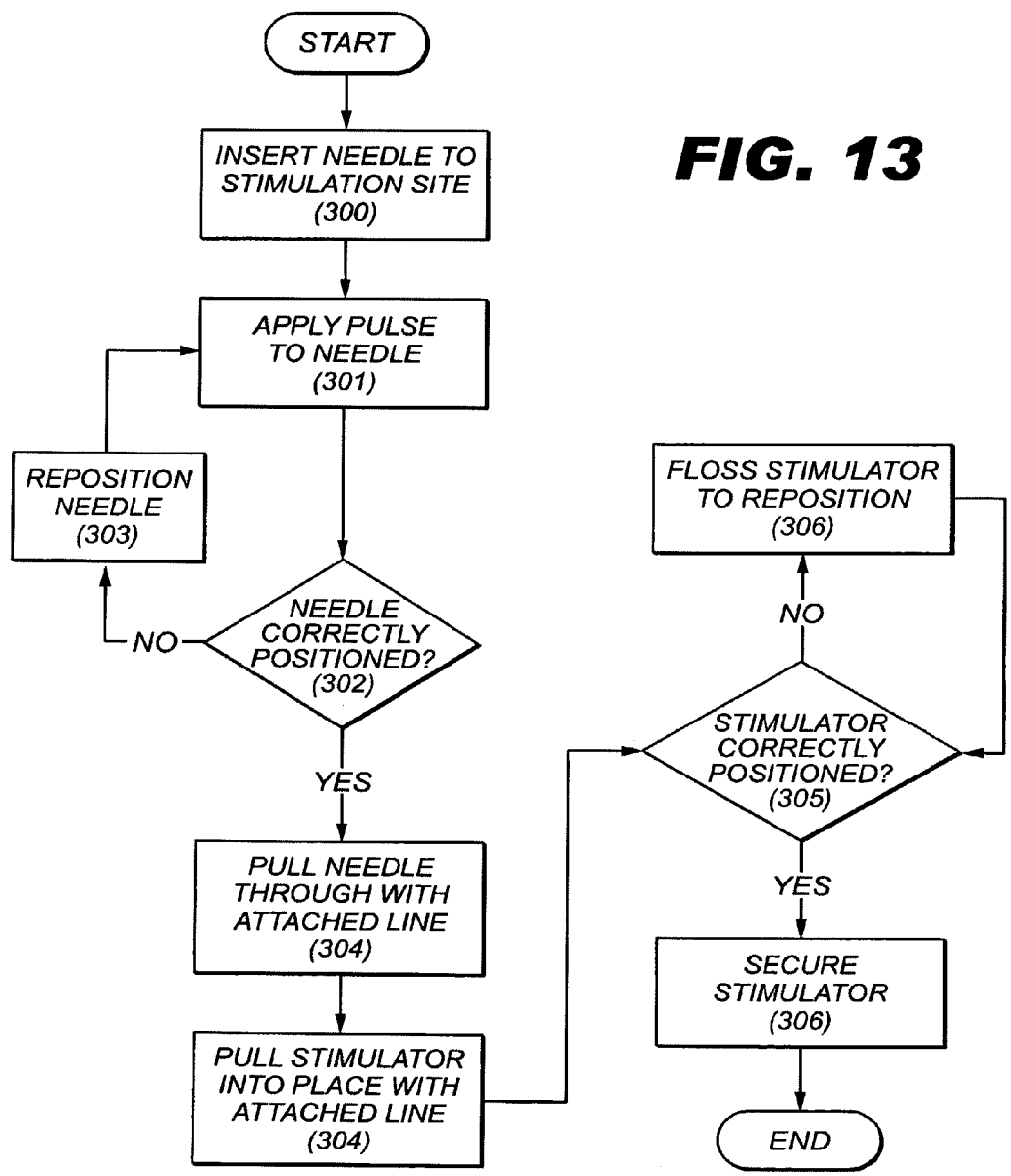
FIG. 13 is a flowchart further illustrating the exemplary method illustrated in FIGS. 10-12 and according to principles described herein.

FIG. 13 is a flowchart illustrating an example of the method described above with respect to FIGS. 10-12. As shown in FIG. 13, a pull-through needle is first inserted at the stimulation site (step 300). The needle is inserted so as to be pass proximal to the tissue to be stimulated and through a location where the stimulator is optimally placed. To determine if the needle has been inserted as intended, a series of pulses or stimulation current may be applied to the needle (step 301). This may be done with the pulse generator and indifferent electrode described above.

By gauging the effect of the electric stimulation delivered via the needle, it can be determined if the needle was positioned within the patient as intended (determination 302). If not, the needle is repositioned (step 303), and the test stimulation is repeated.

Once the needle is confirmed as having passed proximal to the tissue to be stimulated and through the desired site for the stimulator, the needle is pulled through an exit point in the patient's skin (step 304). A line is attached to the needle and follows the needle through the patient's body between the insertion point and exit point.

The stimulator being implanted is attached to this line and pulled into place using the line extending from the needle exit point, as illustrated above (step 304). A second line is attached to the stimulator and continues to extend out through the needle insertion point.

The effect of the stimulator can then be gauged to determine whether the stimulator is, in fact, optimally placed within the patient (determination 305). If the stimulator is not optimally placed, the lines extending from the needle insertion and exit points can be selectively pulled to "floss" the stimulator into the optimal location.

Once the stimulator is optimally positioned (determination 305), the stimulator is secured at that location. This may be accomplished, for example, by suturing or otherwise securing or adhering the lines attached to the stimulator at both the needle insertion point and the needle exit point. In this way, the stimulator will be held at the desired location. Over time, tissue will grow around the stimulator securing it at the desired location. Additionally, as described above, the lines attached to the stimulator may be dissolvable so as to naturally disintegrate with time in the patient's body. As a result, the stimulator is easily placed at a desired target location with great precision and using a minimally invasive procedure.

It will be recognized that the exemplary method of implanting the stimulator (100) described in connection with FIGS. 10-13 is merely illustrative of the many different methods that may be used to implant the stimulator (100). Other methods may include injection, small incision, open placement, laparoscopy, endoscopy, or any other suitable implantation method.

Figure 14:
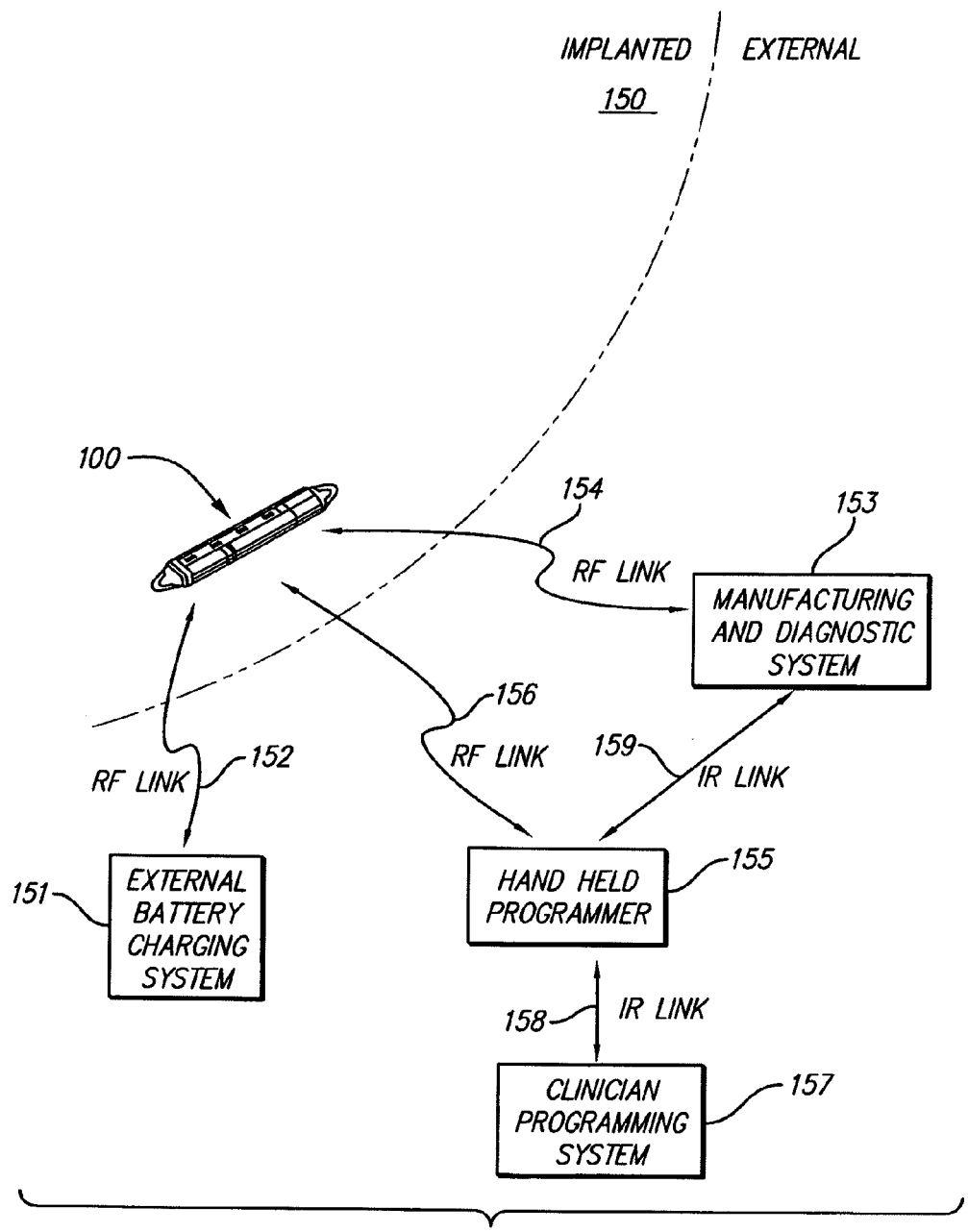
FIG. 14 illustrates various systems and external devices that may be used to support the implanted stimulator according to principles described herein.

FIG. 14 illustrates an exemplary implanted stimulator (100) and examples of the various systems and external devices that may be used to support the implanted stimulator (100). For example, an external battery charging system (EBCS) (151) may provide power used to recharge the battery (145, FIG. 1) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (100) via one or more RF links (154, 156). One or more of these external devices (153, 155, 157) may also be used to control the stimulator (100). For example, the external devices (153, 155, 157) may be used to provide or update the stimulation parameters and other data stored in the programmable memory (146, FIG. 1) of the stimulator (100).

In some cases, two or more of the various illustrated external devices (153, 155, 157) may be used in the treatment of a particular implant patient (150). If multiple external devices are used in the treatment of a patient, there may be some communication among those external devices, as well as with the implanted stimulator (100). For example, the CPS (157) may communicate with the HHP (155) via an infrared (IR) link (158) or via any other suitable communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (100). Furthermore, it will be recognized that the functions performed by the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like, so as to be conveniently placed near the implanted stimulator (100) when in use.

The stimulator (100) of FIG. 14 may be configured to operate independently. Alternatively, as will be described in more detail below, the stimulator (100) may be configured to operate in a coordinated manner with one or more additional stimulators, other implanted devices, or other devices external to the patient's body.

In order to determine the amount and/or type(s) of stimulating drug(s) and/or the strength and/or duration of electrical stimulation required to most effectively treat a particular medical condition, various indicators of the medical condition and/or a patient's response to treatment may be sensed or measured. These indicators include, but are not limited to, muscle or limb activity (e.g., electromyography (EMG)), electrical activity of the brain (e.g., EEG), neurotransmitter levels, hormone levels, and/or medication levels. In some embodiments, the stimulator (100) may be configured to change the stimulation parameters in a closed loop manner in response to these measurements. The stimulator (100) may be configured to perform the measurements. Alternatively, other sensing devices may be configured to perform the measurements and transmit the measured values to the stimulator (100).

Thus, it is seen that one or more external appliances may be provided to interact with the stimulator (100), and may be used to accomplish at least one or more of the following functions:

Function 1: If necessary, transmit electrical power to the stimulator (100) in order to power the stimulator (100) and/or recharge the battery (145, FIG. 1).

Function 2: Transmit data to the stimulator (100) in order to change the stimulation parameters used by the stimulator (100).

Function 3: Receive data indicating the state of the stimulator (100) (e.g., battery level, stimulation parameters, etc.).

Additional functions may include adjusting the stimulation parameters based on information sensed by the stimulator (100) or by other sensing devices.

By way of example, an exemplary method of treating a particular medical condition within a patient may be carried out according to the following sequence of procedures. The steps listed below may be modified, reordered, and/or added to as best serves a particular application.

1. A stimulator (100) is implanted so that its electrodes (142, FIG. 1) and/or infusion outlet (201, FIG. 1) are coupled to or located near a stimulation site. If the stimulator (100) is a microstimulator, such as the BION microstimulator, the microstimulator itself may be coupled to the stimulation site.

2. The stimulator (100) is programmed to apply electrical stimulation to the stimulation site. The stimulator (100) may also be configured to control the operation of a drug delivery system configured to apply drug stimulation to the stimulation site.

3. When the patient desires to invoke electrical, the patient sends a command to the stimulator (100) (e.g., via a remote control) such that the stimulator (100) delivers the prescribed electrical stimulation. The stimulator (100) may be alternatively or additionally configured to automatically apply the electrical stimulation in response to sensed indicators of the particular medical condition.

4. To cease electrical stimulation, the patient may turn off the stimulator (100) (e.g., via a remote control).

5. Periodically, the battery (145, FIG. 1) of the stimulator (100) is recharged, if necessary, in accordance with Function 1 described above.

For the treatment of any of the various types of medical conditions, it may be desirable to modify or adjust the algorithmic functions performed by the implanted and/or external components, as well as the surgical approaches. For example, in some situations, it may be desirable to employ more than one stimulator (100), each of which could be separately controlled by means of a digital address. Multiple channels and/or multiple patterns of electrical stimulation may thereby be used to deal with multiple medical conditions.

Figure 15:
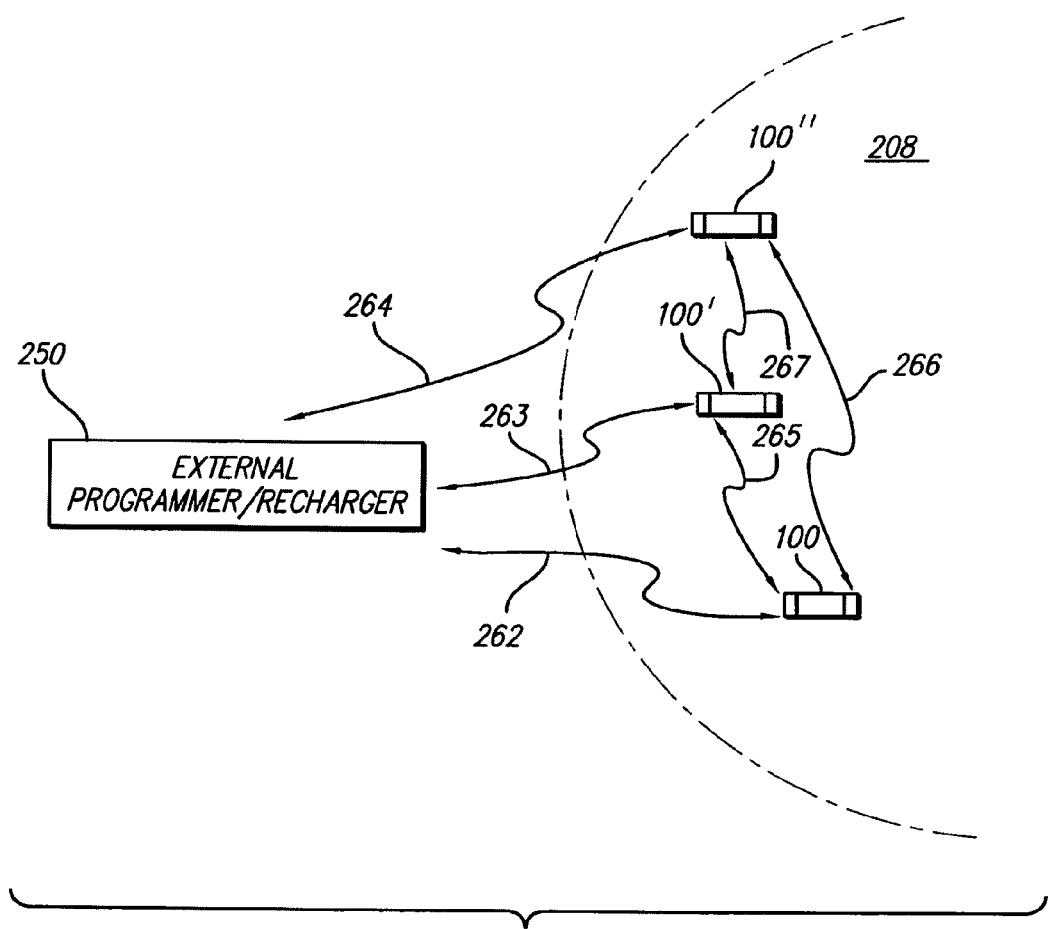
FIG. 15 depicts a number of stimulators configured to communicate with each other and/or with one or more external devices according to principles described herein.

For instance, as shown in the example of FIG. 15, a first stimulator (100) implanted beneath the skin (208) of the patient provides a stimulus to a first location; a second stimulator (100') provides a stimulus to a second location; and a third stimulator (100") provides a stimulus to a third location.

As mentioned earlier, the implanted devices may operate independently or may operate in a coordinated manner with other implanted devices or other devices external to the patient's body. That is, an external controller (250) may be configured to control the operation of each of the implanted devices (100, 100', and 100"). In some embodiments, an implanted device, e.g. stimulator (100), may control or operate under the control of another implanted device(s), e.g. stimulator (100') and/or stimulator (100"). Control lines (262-267) have been drawn in FIG. 15 to illustrate that the external controller (250) may communicate or provide power to any of the implanted devices (100, 100', and 100") and that each of the various implanted devices (100, 100', and 100") may communicate with and, in some instances, control any of the other implanted devices.

As a further example of multiple stimulators (100) operating in a coordinated manner, the first and second stimulators (100, 100') of FIG. 15 may be configured to sense various indicators of a particular medical condition and transmit the measured information to the third stimulator (100"). The third stimulator (100") may then use the measured information to adjust its stimulation parameters and apply electrical stimulation to a stimulation site accordingly.

Alternatively, the external device (250) or other external devices communicating with the external device may be configured to sense various indicators of a patient's condition. The sensed indicators can then be transmitted to the external device (250) or to one or more of the implanted stimulators which may adjust stimulation parameters accordingly. In other examples, the external controller (250) may determine whether any change to stimulation parameters is needed based on the sensed indicators. The external device (250) may then signal a command to one or more of the stimulators to adjust stimulation parameters accordingly.

The stimulator (100; FIG. 2) described herein can be applied in the treatment of a wide variety of different medical, psychiatric, and neurological conditions and/or disorders. A number of these conditions and disorders will now be described below. However, it will be understood that this description is merely exemplary and is not limiting in any way. The stimulator (100; FIG. 2) described herein may be used to treat any condition or disorder where stimulation from an implanted stimulator is helpful to treat the symptoms or cause of the condition or disorder.

For example, the stimulator (100; FIG. 2) described herein may be implanted within a patient's head or neck for the treatment of various conditions and/or disorders such as headaches, facial pain, and/or epilepsy. However, it will be recognized that headaches, facial pain, and epilepsy are merely illustrative of the many different types of medical, psychiatric, and neurological conditions and disorders that exist and may be treated according to the principles described herein.

Epilepsy

Epilepsy is characterized by a tendency to recurrent seizures that can lead to loss of awareness, loss of consciousness, and/or disturbances of movement, autonomic function, sensation (including vision, hearing and taste), mood, and/or mental function. Epilepsy afflicts one to two percent of the population in the developed world. The mean prevalence of active epilepsy (i.e., continuing seizures or the need for treatment) in developed and undeveloped countries combined is estimated to be 7 per 1,000 of the general population, or approximately 40 million people worldwide. Studies in developed countries suggest an annual incidence of epilepsy of approximately 50 per 100,000 of the general population. However, studies in developing countries suggest this figure is nearly double at 100 per 100,000.

Epilepsy is often but not always the result of an underlying brain disease. Any type of brain disease can cause epilepsy, but not all patients with the same brain pathology will develop epilepsy. The cause of epilepsy cannot be determined in a number of patients; however, the most commonly accepted theory posits that it is the result of an imbalance of certain chemicals in the brain, e.g., neurotransmitters. Children and adolescents are more likely to have epilepsy of unknown or genetic origin. The older the patient, the more likely it is that the cause is an underlying brain disease such as a brain tumor or cerebrovascular disease.

Trauma and brain infection can cause epilepsy at any age, and in particular, account for the higher incidence rate in developing countries. For example, in Latin America, neurocysticercosis (cysts on the brain caused by tapeworm infection) is a common cause of epilepsy. In Africa, AIDS and its related infections, malaria and meningitis, are common causes. In India, AIDS, neurocysticercosis and tuberculosis, are common causes. Febrile illness of any kind, whether or not it involves the brain, can trigger seizures in vulnerable young children, which seizures are called febrile convulsions. About 5% of such children go on to develop epilepsy later in life. Furthermore, for any brain disease, only a proportion of sufferers will experience seizures as a symptom of that disease. It is therefore suspected that those who do experience such symptomatic seizures are more vulnerable for similar biochemical/neurotransmitter reasons.

Recent studies in both developed and developing countries have shown that up to 70 percent of newly diagnosed children and adults with epilepsy can be successfully treated (i.e., complete control of seizures for several years) with antiepileptic drugs. After two to five years of successful treatment, drugs can be withdrawn in about 70 percent of children and 60 percent of adults without the patient experiencing relapses. However, up to 30 percent of patients are refractory to medication. There is evidence that the longer the history of epilepsy, the harder it is to control. The presence of an underlying brain disease typically results in a worse prognosis in terms of seizure control. Additionally, partial seizures, especially if associated with brain disease, are more difficult to control than generalized seizures.

Patients suffering from epilepsy may undergo surgery to remove a part of the brain in which the seizures are believed to arise, i.e., the seizure focus. However, in many patients a seizure focus cannot be identified, and in others the focus is in an area that cannot be removed without significant detrimental impact on the patient. For example, in temporal lobe epilepsy, patients may have a seizure focus in the hippocampi bilaterally. However, both hippocampi cannot be removed without adversely affecting a patient's long-term memory. Other patients may have a seizure focus that lies adjacent to a critical area such as the speech center.

Vagus nerve stimulation (VNS) has been applied with partial success in patients with refractory epilepsy. In this procedure, a stimulus may be applied to the left vagus nerve in the neck. Based on a number of studies, approximately five percent of patients undergoing VNS are seizure-free, and an additional 30-40 percent of patients have a greater than 50 percent reduction in seizure frequency.

In addition to this relatively low efficacy, VNS may lead to significant side effects. The vagus nerve provides parasympathetic innervation to the cardiac tissue, and thus VNS may lead to bradycardia, arrhythmia, or even graver cardiac side effects. In fact, VNS systems may only be used on the left vagus nerve, as the right vagus nerve contributes significantly more to cardiac innervation. Additionally, VNS may interfere with proper opening of the vocal cords, which has led to hoarseness and shortness of breath in a significant number of VNS patients.

The exact mechanism of seizure suppression using VNS is unknown. The nucleus of tractus solitarius (NTS; a.k.a., nucleus of the solitary tract) is a primary site at which vagal afferents terminate. Because afferent vagal nerve stimulation has been demonstrated to have anticonvulsant effects, it is likely that changes in synaptic transmission in the NTS can regulate seizure susceptibility. To demonstrate this, Walker, et al. ("Regulation of limbic motor seizures by GABA and glutamate transmission in nucleus tractus solitarius," *Epilepsia*, August 1999) applied muscimol, an agonist of the inhibitory neurotransmitter GABA, to the NTS in a murine model of epilepsy. Muscimol applied to the NTS attenuated seizures in all seizure models tested, whereas muscimol applied to adjacent regions of NTS had no effect. Additionally, biculline methiodide, a GABA antagonist, injected into the NTS did not alter seizure responses. Finally, anticonvulsant effects were also obtained with application of lidocaine, a local anesthetic, into the NTS. Unilateral injections were sufficient to afford seizure protection. Walker, et al. conclude that inhibition of the NTS outputs enhances seizure resistance in the forebrain and provides a potential mechanism for the seizure protection obtained with vagal stimulation.

The NTS sends fibers bilaterally to the reticular formation and hypothalamus, which are important in the reflex control of cardiovascular, respiratory, and gastrointestinal functions. The NTS also provides input to the dorsal motor nucleus of the vagus, which enables the parasympathetic fibers of the vagus nerve to control these reflex responses. The NTS runs the entire length of the medulla oblongata, and the NTS (as well as the trigeminal nuclei) receives somatic sensory input from all cranial nerves, with much of its input coming from the vagus nerve.

Convincing evidence has been given that a significant number of neurons in the trigeminal nerve project to the NTS. By applying horseradish peroxidase to peripheral branches of the trigeminal nerve in a cat, it was found that branches of the trigeminal nerve (the lingual and pterygopalatine nerves) were found to contain fibers which ended ipsilaterally in the rostral portions of the NTS, massively in the medial and ventrolateral NTS, moderately in the intermediate and interstitial NTS, and sparsely in the ventral NTS. (The rostralmost part of the NTS was free from labeled terminals.) After injecting the enzyme into the NTS portions rostral to the area postrema, small neurons were scattered in the maxillary and mandibular divisions of the trigeminal ganglion. It was concluded that trigeminal primary afferent neurons project directly to the NTS. By staining for substance P immunoreactivity, it was found that Substance P containing trigeminal sensory neurons project to the NTS.

Convincing evidence has also been reported that a significant number of neurons in the trigeminal nuclei project to the NTS. Menetrey, et al used the retrograde transport of a protein-gold complex to examine the distribution of spinal cord and trigeminal nucleus caudalis neurons that project to the NTS in the rat. [See Menetrey, et al. "Spinal and trigeminal projections to the nucleus of the solitary tract: a possible substrate for somatovisceral and viscerovisceral reflex activation." *J Comp Neurol* 1987 Jan. 15; 255(3):439-50.] The authors found that retrogradely labeled cells were numerous in the superficial laminae of the trigeminal nucleus caudalis, through its rostrocaudal extent. Since the NTS is an important relay for visceral afferents from both the glossopharyngeal and vagus nerves, the authors suggest that the spinal and trigeminal neurons that project to the NTS may be part of a larger system that integrates somatic and visceral afferent inputs from wide areas of the body. The projections may underlie somatovisceral and/or viscerovisceral reflexes, perhaps with a significant afferent nociceptive component.

Another study utilized microinfusion and retrograde transport of D [3H] aspartate to identify excitatory afferents to the NTS. The authors found that the heaviest labeling was localized bilaterally in the trigeminal nucleus with cells extending through its subdivisions and the entire rostrocaudal axis.

In addition, a study by Fanselow, et al. ("Reduction of pentylenetetrazole-induced seizure activity in awake rats by seizure-triggered trigeminal nerve stimulation," *Journal of Neuroscience*, November 2000) demonstrated that unilateral stimulation via a chronically implanted nerve cuff electrode applied to the infraorbital branch of the trigeminal nerve led to a reduction in electrographic seizure activity of up to 78 percent. The authors reported that bilateral trigeminal stimulation was even more effective.

The thalamus is believed to play a major role in some types of epilepsy by acting as a center for seizure onset or as a relay station in allowing a focal seizure to propagate. In a Single Positron Emission Computed Tomography (SPECT) study of patients with left-sided VNS systems, a consistent decrease of activity was found in the left thalamus caused by VNS. The authors concluded that left-sided VNS reduces seizure onset or propagation through inhibition of the thalamic relay center.

Thalamic relay neurons are essential in generating 3 Hz absence seizures and are believed to be involved in other types of epilepsy. Thalamic nuclei of some patients suffering from epilepsy display neuronal activities described as "low-threshold calcium spike bursts," which have been shown to be related to a state of membrane hyperpolarization of thalamic relay neurons. This thalamic rhythmicity is transmitted to the related cortex, thanks to thalamocortical resonant properties. In the cortex, an asymmetrical corticocortical inhibition (edge effect) at the junction between low and high frequency zones is proposed to be at the origin of a cortical activation of high frequency areas bordering low frequency ones.

Migraine Headache

The mechanism of a migraine is not well understood. Prevalent theories suggest that a migraine is a central nervous system neurovascular disorder and that the trigeminal or occipital nerves may play a prominent role. The trigeminal nerve carries virtually all of the sensation from the face, and thus it likely plays a role in any pain felt at the front or the top of the head.

In "Pathophysiology of migraine—new insights" (*Canadian Journal of Neurological Sciences*, November 1999), Hargreaves, et al. state that "the exact nature of the central dysfunction that is produced in migraines is still not clear and may involve spreading depression-like phenomena and activation of brainstem monoaminergic nuclei that are part of the central autonomic, vascular, and pain control centers. It is generally thought that local vasodilation of intracranial extracerebral blood vessels and a consequent stimulation of surrounding trigeminal sensory nervous pain pathways is a key mechanism underlying the generation of headache pain associated with migraine. This activation of the trigeminovascular system is thought to cause the release of vasoactive sensory neuropeptides, especially CGRP, that increase the pain response. The activated trigeminal nerves convey nociceptive information to central neurons in the brain stem trigeminal sensory nuclei that in turn relay the pain signals to higher centers where headache pain is perceived. It has been hypothesized that these central neurons may become sensitized as a migraine attack progresses." The disorder of migraine may ultimately evoke changes in blood vessels within pain-producing intracranial meningeal structures that give rise to headache pain.

Hargreaves, et al. further state that "the 'triptan' anti-migraine agents (e.g., sumatriptan, rizatriptan, zolmitriptan, and naratriptan) are serotonergic agonists that have been shown to act selectively by causing vasoconstriction through 5 HT1B receptors that are expressed in human intracranial arteries and by inhibiting nociceptive transmission through an action at 5-HT1D receptors on peripheral trigeminal sensory nerve terminals in the meninges and central terminals in brainstem sensory nuclei. These three complementary sites of action underlie the clinical effectiveness of the 5 HT1B/1D agonists against migraine headache pain and its associated symptoms."

In "Current concepts of migraine pathophysiology" (*Canadian Journal of Neurological Sciences*, Autumn 1999), Hamel cites evidence that indicates migraine originates in the brain and, in its process and evolution, affects the meningeal blood vessels and leads to the development of head pain. Hamel states that "this manifestation is related to the activation of the trigeminovascular sensory nerves, which release neuropeptides that mediate vasodilation, and the proinflammatory reaction thought to be involved in pain generation and transmission. Such a concept underscores the fact that the relationship between the nerves and the blood vessels is of paramount importance in the manifestation of the disease's symptoms."

It has also been suggested that primary headache syndromes, such as cluster headache and migraine, share an anatomical and physiologic substrate, namely the neural innervation of the cranial circulation. In "The Trigeminovascular System in Humans: Pathophysiologic Implications for Primary Headache Syndromes of the Neural Influences on the Cerebral Circulation" (*Journal of Cerebral Blood Flow Metabolism*, February 1999), May, et al. report that observations of vasodilation were made in an experimental trigeminal pain study. They conclude that the observed dilation of these vessels in trigeminal pain is not inherent to a specific headache syndrome, but rather is a feature of the trigeminal neural innervation of the cranial circulation. They also state that clinical and animal data suggest that the observed vasodilation is, in part, an effect of a trigeminoparasympathetic reflex. They suggest that the trigeminal innervation of the cranial circulation and the observed vasodilation of the associated vasculature during headache syndromes may be an underlying pathophysiological mechanism of headache.

In "Intraoral Chilling versus Oral Sumatriptan for Acute Migraine" (*Heart Disease*, November-December 2001), Friedman, et al. state that "recent evidence suggests that the primary inflammation occurs in the maxillary nerve segment [of the trigeminal nerve], accessible intraorally. Local tenderness, related to symptom laterality, has been palpated in asymptomatic migraine patients."

In "Cluster Headache" (*Current Treatment Options in Neurology*, November 1999), Salvesen suggests a possible link between the trigeminal nerve and cluster headache: "for a very limited group of patients with chronic cluster headache, surgery may be a last resort. The best surgical options are probably radio-frequency rhizotomy or microvascular decompression of the trigeminal nerve." In a recent study involving eighteen patients, fifteen patients obtained immediate pain relief from chronic intractable cluster headaches after one or two injections of percutaneous retrogasserian glycerol rhizolysis. However, cluster headache recurred in seven patients over the course of the study, suggesting that permanent trigeminal destruction may not be an effective treatment.

For many years, Transcutaneous Electrical Nerve Stimulation (TENS) has been applied with some success to the control of headache and facial pain symptoms. TENS is used to modulate the stimulus transmissions by which pain is felt by applying low-voltage electrical stimulation to large peripheral nerve fibers via electrodes placed on the skin. A study of 282 migraineurs had patients undergo Punctual (i.e., episodic) Transcutaneous Electrical Nerve Stimulation (PuTENS) via pocket electrostimulators. After more than 6 months PuTENS was prophylactically effective in eighty percent of the patients in the study, i.e., their frequency of attacks and use of drugs were reduced by at least fifty percent. However, TENS devices can produce significant discomfort and can only be used intermittently.

The International Headache Society (IHS) published "Classification and Diagnostic Criteria for Headache Disorders, Cranial Neuralgias and Facial Pain" in 1988. IHS identified 13 different general groupings of headache, given below in Table 1.

TABLE 1

Groupings of Headache Disorders and Facial Pain

1) Migraine
2) Tension-type headache
3) Cluster headache and chronic paroxysmal hemicrania
4) Miscellaneous headaches unassociated with structural lesions
5) Headache associated with head trauma
6) Headache associated with vascular disorders
7) Headache associated with non-vascular intracranial disorder
8) Headache associated with substances or their withdrawal
9) Headache associated with non-cephalic infections
10) Headaches associated with metabolic disorders
11) Headache or facial pain associated with disorder of cranium, neck, eyes, ears, nose, sinuses, teeth, mouth or other facial or cranial structures
12) Cranial neuralgias, nerve trunk pain and deafferentation pain
13) Non-classifiable headache The IHS classification of the most common types of headache is summarized in Table 2 below.

TABLE 2

IHS Classification of Primary Headaches

| | |
|---|---|
| 1. | Migraine |
| 1.1 | Migraine without aura |
| 1.2 | Migraine with aura |
| 1.2.1 | Migraine with typical aura |
| 1.2.2 | Migraine with prolonged aura |
| 1.2.3 | Familial hemiplegic migraine headache |
| 1.2.4 | Basilar migraine |
| 1.2.5 | Migraine aura without headache |
| 1.2.6 | Migraine with acute onset aura |
| 1.3 | Ophthalmoplegic migraine |
| 1.4 | Retinal migraine |
| 1.5 | Childhood periodic syndromes that may be precursors to or associated with migraine |
| 1.5.1 | Benign paroxysmal vertigo of childhood |
| 1.5.2 | Alternating hemiplegia of childhood |
| 1.6 | Complications of migraine |
| 1.6.1 | Status migrainosus |
| 1.6.2 | Migrainous infarction |
| 1.7 | Migrainous disorder not fulfilling above criteria |
| 2. | Tension-type headache |
| 2.1 | Episodic tension-type headache |
| 2.1.1 | Episodic tension-type headache associated with disorder of pericranial muscles |

TABLE 2-continued

IHS Classification of Primary Headaches

| | |
|---|---|
| 2.1.2 | Episodic tension-type headache not associated with disorder of pericranial muscles |
| 2.2 | Chronic tension-type headache |
| 2.2.1 | Chronic tension-type headache associated with disorder of pericranial muscles |
| 2.2.2 | Chronic tension-type headache not associated with disorder of pericranial muscles |
| 2.3 | Headache of the tension-type not fulfilling above criteria |
| 3. | Cluster headache and chronic paroxysmal hemicrania |
| 3.1 | Cluster Headache |
| 3.1.1 | Cluster headache, periodicity undetermined |
| 3.1.2 | Episodic cluster headache |
| 3.1.3. | Chronic Cluster Headache |
| 3.1.3.1 | Unremitting from onset |
| 3.1.3.2 | Evolved from episodic |
| 3.2 | Chronic paroxysmal hemicrania |
| 3.3 | Cluster headache-like disorder not fulfilling above Criteria |

The IHS classification provides diagnostic criteria for migraine without and with aura, summarized in Tables 3 and 4 below.

TABLE 3

IHS Diagnostic Criteria for Migraine Without Aura

| | |
|---|---|
| A. | At least five attacks fulfilling B-D below: |
| B. | Headache attacks lasting 4-72 hours (untreated or unsuccessfully treated) |
| C. | Headache has at least two of the following characteristics:<br>1. Unilateral location<br>2. Pulsating quality<br>3. Moderate or severe intensity (inhibits or prohibits daily activities)<br>4. Aggravation by walking stairs or similar routine physical activity |
| D. | During headache at least one of the following:<br>1. Nausea and/or vomiting<br>2. Photophobia and phonophobia |
| E. | At least one of the following:<br>1. History and physical do not suggest headaches secondary to organic or systemic metabolic disease<br>2. History and/or physical and/or neurologic examinations do suggest such disorder, but is ruled out by appropriate investigations<br>3. Such disorder is present, but migraine attacks do not occur for the first time in close temporal relation to the disorder |

TABLE 4

IHS Diagnostic Criteria for Migraine With Aura

| | |
|---|---|
| A. | At least two attacks fulfilling B below: |
| B. | At least three of the following four characteristics:<br>1. One or more fully reversible aura symptoms indicating focal cerebral cortical and/or brain stem dysfunction<br>2. At least one aura symptom develops gradually over more than four minutes or two or more symptoms occur in succession<br>3. No aura symptom lasts more than 60 minutes. If more than one aura symptom is present, accepted duration is proportionally increased<br>4. Headache follows aura with a free interval of less than 60 minutes. It may also begin before or simultaneously with the aura. |
| C. | At least one of the following:<br>1. History and physical and neurologic examinations do not suggest headaches secondary to organic or systemic metabolic disease<br>2. History and/or physical and/or neurologic examinations do suggest such disorder, but it is ruled out by appropriate investigations |

TABLE 4-continued

IHS Diagnostic Criteria for Migraine With Aura

3. Such disorder is present, but migraine attacks do not occur for the first time in close temporal relation to the disorder The IHS classification includes several different types of migraine variants. Basilar migraine is defined as a migraine with an aura involving the brainstem. Symptoms include ataxia, dysarthria, vertigo, tinnitus and/or changes in consciousness and cognition. Ophthalmoplegic migraine is associated with acute attacks of third nerve palsy with accompanying dilation of the pupil. In this setting, the differential diagnosis includes an intracranial aneurysm or chronic sinusitis complicated by a mucocele. The ophthalmoplegia can last from hours to months. Hemiplegic migraine is distinguished by the accompanying hemiplegia, which can be part of the aura, or the headache may precede the onset of hemiplegia. Hemiplegic migraine can be familial and may last for days or weeks, clinically simulating a stroke. An additional differential diagnosis includes focal seizures.

Status migrainosus describes a migraine lasting longer than 72 hours with intractable debilitating pain, and typically occurs in a setting of inappropriate and prolonged use of abortive anti-migraine drugs. These patients may require hospitalization, both for pain control, detoxification from the abused drugs, and treatment of dehydration resulting from prolonged nausea and vomiting.

A migraine prevalence survey of American households was conducted in 1992, and included 20,468 respondents 12-80 years of age. Using a self-administered questionnaire based on modified IHS criteria, 17.6% of females and 5.7% of males were found to have one or more migraine headaches per year. A projection to the total US population suggests that 8.7 million females and 2.6 million males suffer from migraine headache with moderate to severe disability. Of these, 3.4 million females and 1.1 million males experience one or more attacks per month. Prevalence is highest between the ages of 25 and 55, during the peak productive years.

Based on published data, the Baltimore County Migraine Study, MEDSTAT's MarketScan medical claims data set, and statistics from the Census Bureau and the Bureau of Labor Statistics, it has been estimated that migraineurs require 3.8 bed rest days for men and 5.6 days for women each year, resulting in a total of 112 million bedridden days. Migraine costs American employers about $13 billion a year because of missed workdays and impaired work function—close to $8 billion is directly due to missed workdays. Patients of both sexes aged 30 to 49 years incurred higher indirect costs compared with younger or older employed patients. Annual direct medical costs for migraine care are about $1 billion, with about $100 spent per diagnosed patient. Physician office visits account for about 60% of all costs; in contrast, emergency department visits contribute less than 1% of the direct costs.

Tension-Type Headache

The diagnostic criteria for tension-type headaches are summarized in Table 5 below. However, migraine symptoms may overlap considerably with those of tension-type headaches. Tension-type headaches are believed by some experts to be a mild variant of migraine headache. Patients with tension-type headaches who also have migraines may experience nausea and vomiting with a tension headache, though when they do, it typically is mild and for a shorter duration compared to that with a migraine. Tension-type headache may be a disorder unto itself in individuals who do not have migraines, and may manifest as attacks of mild migraine in individuals with migraines.

TABLE 5

IHS Criteria for Various Forms of Tension-Type Headache

Tension-type headache

At least two of the following pain characteristics:
1. Pressing/tightening (non-pulsating) quality
2. Mild or moderate intensity (may inhibit, but does not prohibit activities)
3. Bilateral location
4. No aggravation by walking stairs or similar routine physical activity Both of the following:
1. No nausea or vomiting (anorexia may occur)
2. Photophobia and phonophobia absent, or only one is present At least one of the following:
1. History and physical do not suggest headaches secondary to organic or systemic metabolic disease
2. History and/or physical and/or neurologic examinations do suggest such disorder, but is ruled out by appropriate investigations
3. Such disorder is present, but tension-type headache does not occur for the first time in close temporal relation to the disorder Episodic tension-type headache (ETTH)

Diagnostic criteria:
A. At least 10 previous episodes, <180 days/year (<15/mo) with headache
B. Headache lasting from 30 minutes to 7 days Chronic tension-type headache (CTTH)

Diagnostic criteria:
A. Average frequency ≥1 day/month (≥189 days/year) for ≥6 months Tension-type headache associated with disorder of pericranial muscles At least one of the following:
1. Increased tenderness of pericranial muscles demonstrated by manual palpation or pressure algometer.
2. Increased electromyographic level of pericranial muscles at rest or during physiologic tests.

Tension-type headache not associated with pericranial muscle disorder

No increased tenderness of pericranial muscles. If studied, electromyography of pericranial muscles shows normal levels of activity.

Based on a telephone survey of 13,345 people, the 1-year period prevalence of episodic tension-type headache (ETTH) is estimated to be 38.3%, according to IHS criteria. Women had a higher 1-year ETTH prevalence than men in all age, race, and education groups, with an overall prevalence ratio of 1.16. Prevalence peaked in the 30- to 39-year-old age group in both men (42.3%) and women (46.9%). Prevalence increased with increasing educational levels in both sexes, reaching a peak in subjects with graduate school educations of 48.5% for men and 48.9% for women. Of subjects with ETTH, 8.3% reported lost workdays because of their headaches, while 43.6% reported decreased effectiveness at work, home, or school.

Chronic Daily Headache

Chronic tension-type headache (CTTH) is a subtype of tension headaches, with patients experiencing headaches daily or almost every day. In practice, the term "chronic daily headache" is commonly used to describe headaches lasting for greater than 4 hours per day and for at least 15 days per month. The classification of chronic daily headaches is summarized below in Table 6.

TABLE 6

Classification of Chronic Daily Headache

Transformed migraine

1. With medication overuse
2. Without medication overuse

Chronic tension-type headache (CTTH)

1. With medication overuse
2. Without medication overuse

New daily persistent headache

1. With medication overuse
2. Without medication overuse

Hemicrania continua

1. With medication overuse
2. Without medication overuse

In the study of 13,345 people cited above, the 1-year period prevalence of chronic tension-type headache (CTTH) was estimated to be 2.2%. This prevalence was higher in women and declined with increasing education. Subjects with CTTH reported more lost workdays (mean of 27.4 days vs. 8.9 days for those reporting lost workdays) and reduced-effectiveness days (mean of 20.4 vs. 5.0 days for those reporting reduced effectiveness) compared with subjects with ETTH.

Chronic daily headaches are best conceptualized as an umbrella category term referring to a group of headache disorders characterized by headaches which occur greater than 15 days per month, with an average untreated duration of greater than 4 hours per day. There are many secondary causes of chronic daily headache, including post-traumatic headache, arthritis, intracranial mass lesions, etc. There are also short-lived primary headache disorders that occur greater than 15 days per month, such as chronic cluster headache or the paroxysmal hemicranias. The most common primary, chronic daily headache disorders include transformed migraine, chronic tension-type headaches, new daily persistent headache, or hemicrania continua. Each of these diagnoses can be complicated by medication overuse (e.g., barbiturates, acetaminophen, aspirin, caffeine, ergotamine tartrate and opioids). When used daily, all of these medications can lead to a vicious cycle of rebound headaches.

Cluster Headache

The 1988 IHS classification system recognized the uniqueness of cluster headache as a clinical and epidemiological entity. Formerly classified as a vascular migraine variant, cluster headache (a.k.a. suicide headache) is thought to be one of the most severe headache syndromes. It is characterized by attacks of severe pain, generally unilateral and orbital and lasting 15 minutes to 3 hours, with one or more symptoms such as unilateral rhinorrhea, nasal congestion, lacrimation, and conjunctival injection. In most patients, headaches occur in episodes, generally with a regular time pattern. These "cluster periods" last for weeks to months, separated by periods of remission lasting months to years. These headaches primarily affect men and in many cases patients having distinguishing facial, body, and psychological features. Several factors may precipitate cluster headaches, including histamine, nitroglycerin, alcohol, transition from rapid eye movement (REM) to non-REM sleep, circadian periodicity, environmental alterations, and change in the level of physical, emotional, or mental activity. The IHS classification system gives specific diagnostic criteria for cluster headache, as given in Table 7 below.

TABLE 7

IHS Diagnostic Criteria for Cluster Headache

| 3.1 | Cluster Headache |
| A. | At least 5 attacks fulfilling B-D below: |
| B. | Severe unilateral, orbital, supraorbital and/or temporal pain lasting 15-180 minutes untreated |
| C. | At least one of the following signs present on the pain side: |
| | 1. Conjunctival injection |
| | 2. Lacrimation |
| | 3. Nasal congestion |
| | 4. Rhinorrhea |
| | 5. Forehead and facial sweating |
| | 6. Miosis |
| | 7. Ptosis |
| | 8. Eyelid edema |
| D. | Frequency of attacks: from 1 every other day to 8 per day |
| E. | At least one of the following: |
| | 1. History, physical and neurological examinations do not suggest one of the disorders listed in groups 5-11 of Table 1 |
| | 2. History and/or physical and/or neurological examinations do suggest such disorder, but it is ruled out by appropriate investigations |
| | 3. Such disorder is present, but cluster headache does not occur for the first time in close temporal relation to the disorder |
| 3.1.1 | Cluster headache periodicity undefined |
| | A. Criteria for 3.1 fulfilled |
| | B. Too early to classify as 3.1.2 or 3.1.3 |
| 3.1.2 | Episodic cluster headache |
| | Description: Attacks lasting between 1 week and 3 months occur in periods lasting 1 week to one year separated by pain free periods lasting 14 days or more. |
| | A. All the letter headings of 3.1 |
| | B. At least 2 periods of headaches (cluster periods) lasting (untreated) from 7 days to one year, separated by remissions of at least 14 days. |
| 3.1.3 | Chronic cluster headache |
| | Description: Attacks lasting between 2 weeks and 3 months occur for more than one year without remission or with remissions lasting less than 14 days. |
| | A. All the letter headings of 3.1 |
| | B. Absence of remission phases for one year or more or with remissions lasting less than 14 days. |
| 3.1.3.1 | Chronic cluster headache unremitting from onset |
| | A. All the letter headings of 3.1.3 |
| | B. Absence of remission periods lasting 14 days or more from onset. |
| 3.1.3.2 | Chronic cluster headache evolved from episodic |
| | A. All the letter headings of 3.1.3 |
| | B. At least one interim remission period lasting 14 days or more within one year after onset, followed by unremitting course for at least one year. |

The estimated prevalence of cluster headache is 69 cases per 100,000 people. Men are affected more commonly than women in a proportion of 6:1. Although most patients begin experiencing headache between the ages of 20 and 50 years (mean of 30 years), the syndrome may begin as early as the first decade and as late as the eighth decade.

Cervicogenic Headache

Cervicogenic headache (CEH) is a headache with its origin in the neck area. The source of pain is in structures around the neck that have been damaged. These structures can include joints, ligaments, muscles, and cervical discs, all of which have complex nerve endings. When these structures are damaged, the nerve endings send pain signals up the pathway from the upper nerves of the neck to the brainstem. These nerve fibers may synapse in the same brainstem nuclei as the nerve fibers of the trigeminal nerve. Since the trigeminal nerve is responsible for the perception of head pain, the patient experiences the symptoms of headache and/or facial pain.

While many patients who are diagnosed with CEH have the traditional symptoms of tension-type headache, some of the patients who have the traditional symptoms of migraine and cluster headache also respond to CEH diagnosis and treatment.

Facial Pain

Facial pain may be due to a number of underlying disorders. Among the most common is Trigeminal Neuralgia (also known as tic douloureux). More than 50,000 people in the United States suffer from trigeminal neuralgia. This disorder may cause episodes of intense, stabbing, electric shock-like pain in the areas of the face where the branches of the nerve are distributed (e.g., the lips, eyes, nose, scalp, forehead, upper jaw, and lower jaw). A less common form of the disorder, Atypical Trigeminal Neuralgia, may cause less intense, constant, dull burning or aching pain, sometimes with occasional electric shock-like stabs. Both forms of the disorder most often affect one side of the face, but some patients experience pain at different times on both sides. Onset of symptoms occurs most often after age 50, and it affects women more often than men. For patients with this disorder, an ordinary touch of the face, such as when brushing teeth or applying makeup, can trigger an attack. Trigeminal neuralgia is believed to be due to hyper-excitability of fibers of the trigeminal nerve or its ganglion. Microelectrode recordings from the trigeminal ganglion have demonstrated sustained high-frequency bursts during pain episodes of trigeminal neuralgia.

Trigeminal neuralgia may be treated medically with drugs that decrease neural excitability, e.g., carbamazepine or phenytoin. However, such medications prove ineffective for many patients over the course of the disease. Thus, a number of surgical interventions (e.g., microvascular decompression of the trigeminal ganglion or it nerve fibers, radio-frequency rhizotomy) have been developed.

Another cause of facial pain is Temporomandibular Joint (TMJ) Dysfunction Syndrome. Most TMJ discomfort is temporary and can be treated with inexpensive remedies. However, some TMJ dysfunction patients are afflicted with persistent and sometimes unbearable pain. The symptoms of this chronic dysfunction include persistent pain in the facial muscles on one or both sides, a clicking or popping sensation when opening the mouth or working the jaw, recurring headaches, and difficulty chewing. Analgesics and anti-inflammatory medication may relieve the pain in some patients. Others turn to TMJ surgery in desperation.

Yet another cause of facial pain is Postherpetic Neuralgia, which is a possible complication of herpes zoster reactivation ("shingles"). The herpes zoster virus may cause chicken pox upon initial infection. When reactivated, the virus causes shingles—a painful disease characterized by eruptions along a nerve path often accompanied by severe neuralgia and a skin rash. It can affect the torso or limbs (spinal ganglia shingles) or the face (trigeminal ganglia shingles). Approximately one in five adults develops shingles, usually after age 50. For most people, shingles is an acute condition with pain typically lasting one month. However, in older patients or patients with a compromised immune system, singles can lead to postherpetic neuralgia, a very painful chronic condition in which the pain associated with the shingles persists beyond one month, even after the rash is gone. The incidence of postherpetic neuralgia is almost negligible before age 50, but at least 50% of patients older than 60 years and almost 75% beyond age 70 become affected following a shingles attack. Postherpetic neuralgia tends to improve over time without treatment. Some estimates suggest that only two to three percent of patients have pain lasting more than one year. However, since more than 60,000 new cases develop annually in the US, the collective morbidity is still substantial. Treatment of postherpetic neuralgia consists of symptomatic relief of severe pain with tricyclic antidepressants and opioids.

Other Medical, Psychiatric, and Neurological Conditions and Disorders

Other medical, psychiatric, and neurological conditions and/or disorders that may be treated with the stimulator (100; FIG. 2) described herein include, but are not limited to, the following:

1) Pain resulting from one or more medical conditions including, but not limited to: migraine headaches, including but not limited to migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; musculoskeletal neck pain; reflex sympathetic dystrophy, cervicalgia; glossodynia, carotidynia; cricoidynia; otalgia due to middle ear lesion; gastric pain; sciatica; maxillary neuralgia; laryngeal pain, myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia.

2) Epilepsy, including, but not limited to, generalized and partial seizure disorders.

3) Cerebrovascular diseases resulting from one or more medical conditions including, but not limited to, atherosclerosis, aneurysms, strokes, and cerebral hemorrhage.

4) Autoimmune diseases resulting from one or more medical conditions including, but not limited to, multiple sclerosis.

5) Sleep disorders resulting from one or more medical conditions including, but not limited to, sleep apnea and parasomnias.

6) Autonomic disorders resulting from one or more medical conditions including, but not limited to: gastrointestinal disorders, including, but not limited to, gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including, but not limited to, cardiac dysrythmias and arrythmias, hypertension, and carotid sinus disease.

7) Urinary bladder disorders resulting from one or more medical conditions including, but not limited to, spastic and flaccid bladder.

8) Abnormal metabolic states resulting from one or more medical conditions including, but not limited to, hyperthyroidism and hypothyroidism.

9) Disorders of the muscular system resulting from one or more medical conditions including, but not limited to, muscular dystrophy and spasms of the upper respiratory tract and face.

10) Neuropsychiatric disorders resulting from one or more medical conditions including, but not limited to, depression, schizophrenia, bipolar disorder, autism, personality disorders, and obsessive-compulsive disorder.

11) Urinary and fecal incontinence.

12) Erectile or other sexual dysfunctions.

For ease of explanation, the term "medical condition" will be used herein and in the appended claims, unless otherwise specifically denoted, to refer to any medical, psychiatric, and/or neurological condition and/or disorder described herein, listed above, or related or similar to any condition or disorder described or listed herein.

Figure 16:
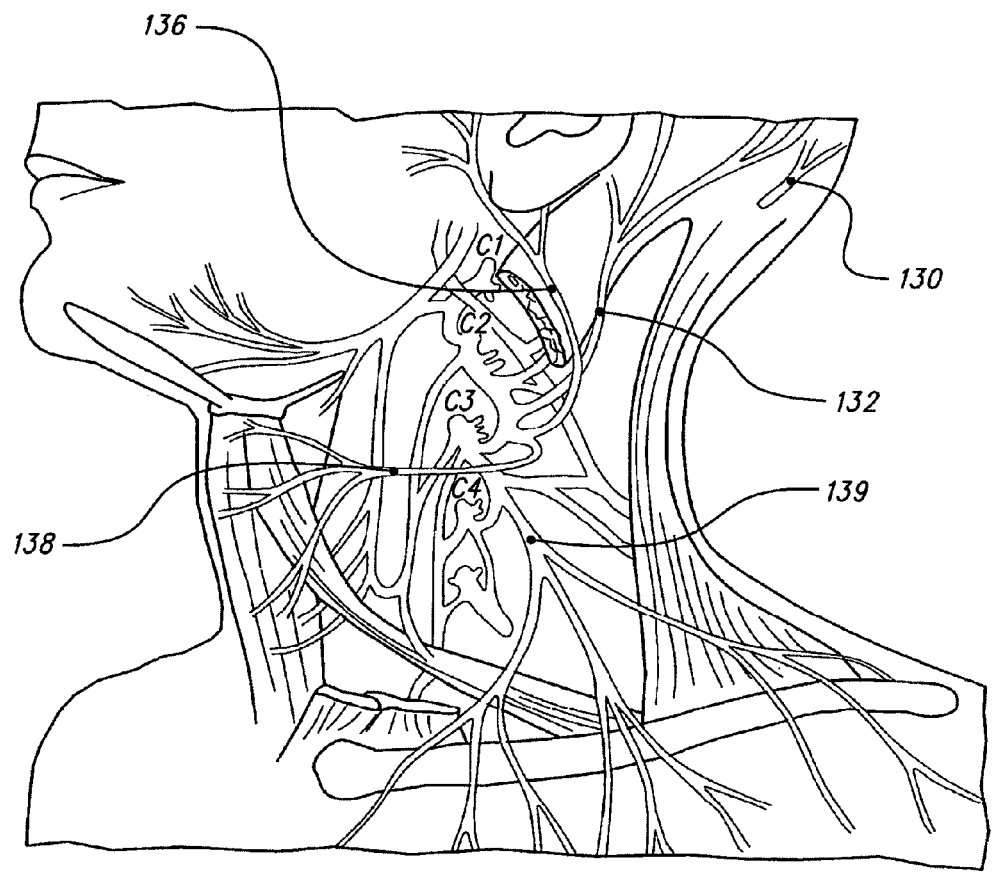
FIG. 16 depicts the upper cervical spine area of a patient and shows a number of nerves originating in the upper cervical spine area that can be stimulated with an implanted stimulator according to principles described herein.
Figure 17:
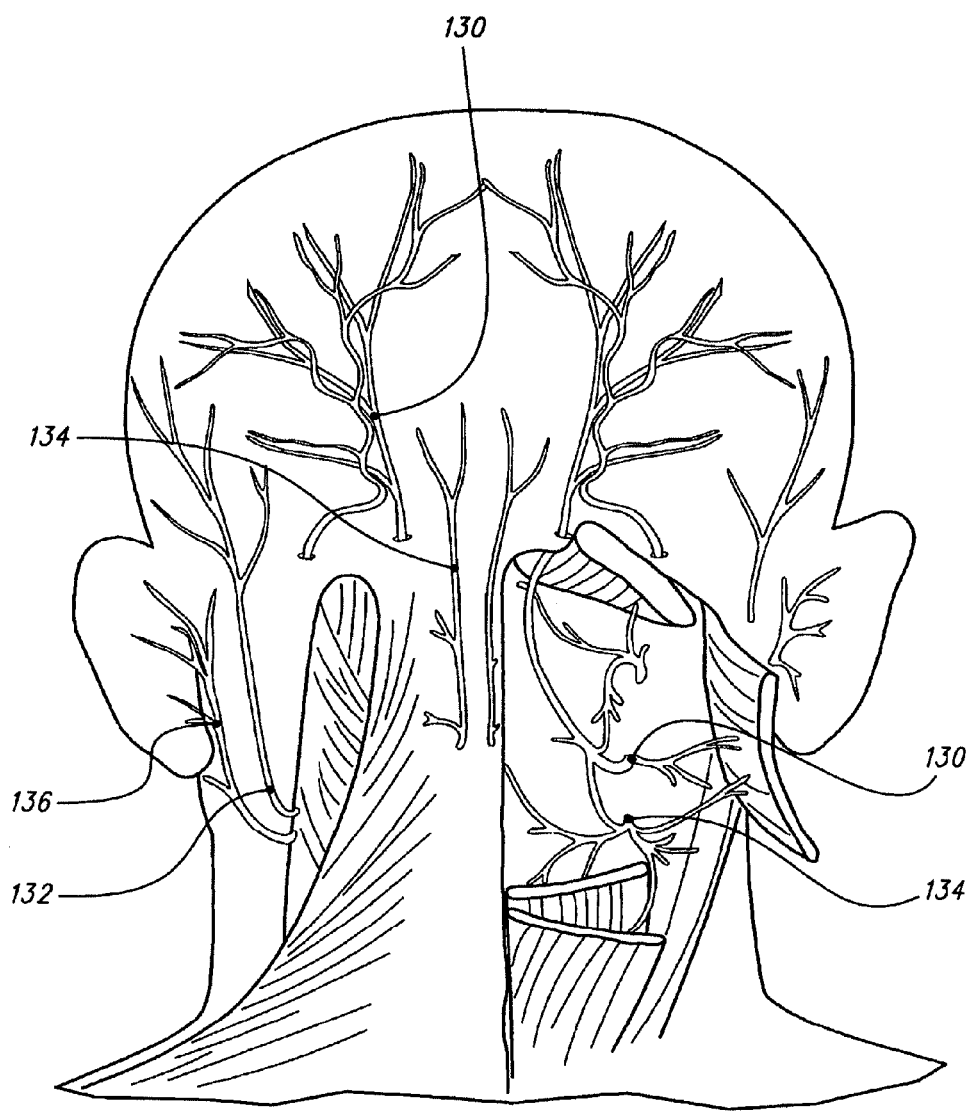
FIG. 17 shows various nerves in the back of the head and neck that can be stimulated with an implanted stimulator according to principles described herein.

FIGS. 16 and 17 depict the upper cervical spine (C1-C4) area of a patient. As shown in FIGS. 16 and 17, a number of nerves arise from the upper cervical spine (C1-C4). Examples of such nerves include, but are not limited to, the greater occipital nerve(s) (130), the lesser occipital nerve(s) (132), the third occipital nerve(s) (134), greater auricular nerve(s) (136), transverse cervical nerve(s) (138), the supraclavicular nerve(s) (139), and/or branches of any of these nerves. As shown in FIG. 17, the occipital nerves (130, 132, 134) are relatively easily accessed, especially in their distal portions, since they lie subcutaneously in the back of the head and upper neck.

In some embodiments, at least one stimulus is applied with the stimulator (100; FIG. 2) described herein to one or more target nerves within a patient to treat and/or prevent one or more of the medical conditions listed above. The target nerve may be, for example, any nerve originating in the upper cervical spine area (i.e., C1-C4) or any branch of a nerve originating in the upper cervical spine area. For example, the target nerve may include, but is not limited to, the greater occipital nerve(s) (130), the lesser occipital nerve(s) (132), the third occipital nerve(s) (134), greater auricular nerve(s) (136), transverse cervical nerve(s) (138), the supraclavicular nerve(s) (139), and/or branches of any of these nerves. The greater (130), lesser (132), and third occipital nerves (134), as well as the greater auricular nerves (136), are relatively easily accessed, especially in their distal portions, since they lie subcutaneously in the back of the head and upper neck. The stimulator (100; FIG. 2) may thus be easily implanted adjacent to one or more of these nerves and then optimally positioned using the systems and methods described herein. A more complicated surgical procedure may be required for sufficient access to one or more of these nerves and/or for purposes of fixing the stimulator in place. The sites of injection or skin incision may be selected such that the resulting scars would likely be covered by hair on most people.

It will be recognized that the stimulus may be applied with the stimulator (100; FIG. 2) to any nerve, tissue, organ, or other stimulation site within the patient to treat any of the above listed medical conditions. For example, urinary incontinence may be treated by stimulating the nerve fibers proximal to the pudendal nerves of the pelvic floor. Erectile or other sexual dysfunctions may be treated by providing stimulation of the cavernous nerve(s). Other disorders, e.g., neurological disorders caused by injury or stroke, may be treated by providing stimulation to other appropriate nerve(s).

The preceding description has been presented only to illustrate and describe embodiments of the invention. It is not intended to be exhaustive or to limit the invention to any precise form disclosed. Many modifications and variations are possible in light of the above teaching.

What is claimed is:

1. An implantable stimulator comprising:
a casing defining an interior cavity;
a plurality of discrete electrodes disposed on an outer surface of the casing;
stimulation circuitry housed in the interior cavity defined by the casing; and
at least one electrical conductor coupling the discrete electrodes to the stimulation circuitry housed in the interior cavity, wherein at least a portion of the at least one electrical conductor extends along the outer surface of the casing to reach the discrete electrodes.

2. The implantable stimulator of claim 1, wherein the at least one electrical conductor comprises a plurality of electrical conductors respectively coupling the discrete electrodes to the stimulation circuitry housed in the interior cavity.

3. The implantable stimulator of claim 2, further comprising an electrical insulator on which at least portions of the plurality of electrical conductors are disposed.

4. The implantable stimulator of claim 3, wherein the electrical insulator comprises an insulator film.

5. The implantable stimulator of claim 1, wherein the casing is an elongate casing.

6. The implantable stimulator of claim 5, wherein the outer surface of the elongate casing has asymmetric lateral sections effective to hinder rotation of the implantable stimulator within a patient.

7. The implantable stimulator of claim 6, wherein:
the asymmetric lateral sections are generally rounded rectangular; and
the discrete electrodes are each dimensioned to occupy a portion of a long side of the generally rounded rectangular lateral sections.

8. The implantable stimulator claim 1, wherein the stimulation circuitry is adjustable to deliver electrical stimulus to a site within a patient via one or more of the discrete electrodes.

9. The implantable stimulator of claim 1, further comprising a feed through assembly coupled to the casing, the feed through assembly comprising a number of conductive feed throughs that electrically couple the stimulation circuitry housed within the casing to the electrodes.

10. The implantable stimulator of claim 9, further comprising:
a first connecting band hermetically coupled to an end of the casing;
a second connecting band hermetically coupled to an end of the feed through assembly, wherein the first connecting band and the second connecting band are hermetically coupled to each other.

11. The implantable stimulator of claim 1, further comprising a battery coupled to the elongate casing, the battery configured to provide power for the stimulation circuitry housed within the casing.

12. The implantable stimulator of claim 11, further comprising:
a first connecting band coupled to an end of the casing; and
a second connecting band coupled to an end of the battery, wherein the first connecting band and the second connecting band are hermetically coupled to each other.

13. The implantable stimulator of claim 1, further comprising an indifferent electrode for completing one or more stimulation circuits.

14. The implantable stimulator of claim 1, wherein the casing comprises a material configured to allow passage of a magnetic field.

15. The implantable stimulator of claim 1, wherein the casing is composed of a ceramic material.

16. The implantable stimulator of claim 1, wherein the stimulation circuitry housed within the casing comprises:
a programmable memory unit storing one or more stimulation parameters; and electrical circuitry configured to generate an electrical stimulus.

17. The implantable stimulator of claim 16, further comprising a sensor device for sensing at least one parameter related to a medical condition of a patient, wherein the stimulation circuitry is configured to adjust the electrical stimulus based on the one or more stimulation parameters.

18. The implantable stimulator of claim 1, wherein the outer surface of the casing has a shape effective to hinder rotation of the implantable stimulator within a patient.

19. The implantable stimulator of claim 1, wherein the shape of the casing is non-cylindrical.

20. The implantable stimulator of claim 1, wherein a height of the implantable stimulator is equal to or less than 4.25 millimeters, a width of the implantable stimulator is equal to or less than 7.25 millimeters, and a length of the implantable stimulator is equal to or less than 28 millimeters.

* * * * *